(12) United States Patent
Brady et al.

(10) Patent No.: US 6,258,308 B1
(45) Date of Patent: Jul. 10, 2001

(54) PROCESS FOR ADJUSTING WVTR AND OTHER PROPERTIES OF A POLYOLEFIN FILM

(75) Inventors: Kevin A. Brady, Cary; John H. Mackay, Lake Zurich, both of IL (US)

(73) Assignee: Exxon Chemical Patents Inc., Baytown, TX (US)

( * ) Notice: Subject to any disclaimer, the term of this patent is extended or adjusted under 35 U.S.C. 154(b) by 0 days.

(21) Appl. No.: 09/312,103

(22) Filed: May 14, 1999

Related U.S. Application Data

(63) Continuation-in-part of application No. 08/690,136, filed on Jul. 31, 1996.
(60) Provisional application No. 60/104,452, filed on Oct. 16, 1998, provisional application No. 60/104,455, filed on Oct. 16, 1998, provisional application No. 60/104,948, filed on Oct. 20, 1998, and provisional application No. 60/104,985, filed on Oct. 20, 1998.

(51) Int. Cl.[7] ............................. B29C 47/88; B29C 55/18
(52) U.S. Cl. .................................... 264/210.2; 264/288.8; 428/500
(58) Field of Search ................................. 264/210.2, 154, 264/288.8, DIG. 47; 156/244.18, 206; 428/156, 163, 174, 175, 181, 308.4, 315.9, 516, 500; 442/290, 398

(56) References Cited

U.S. PATENT DOCUMENTS

| Re. 28,606 | 11/1975 | Ikeda et al. ........................ 428/155 |
| Re. 28,608 | 11/1975 | Dixon ................................. 29/211 R |
| 2,896,626 | 7/1959 | Voigtman ............................ 128/287 |
| 3,233,029 | 2/1966 | Rasmussen .......................... 264/288 |
| 3,299,174 | 1/1967 | Kuhre et al. ........................ 260/876 |
| 3,378,512 | 4/1968 | Hamed et al. ...................... 260/33.6 |

(List continued on next page.)

FOREIGN PATENT DOCUMENTS

| 577644 | 9/1988 | (AU) . |
| 621048 | 4/1989 | (AU) . |
| 1296225 | 2/1992 | (CA) . |
| 1311181 | 12/1992 | (CA) . |
| 1322082 | 9/1993 | (CA) . |
| 2144737 | 3/1994 | (CA) . |

(List continued on next page.)

OTHER PUBLICATIONS

Karen K. Leonas "Evaluation of five nonwoven surgical gowns as barriers to liquid strikethrough and bacterial transmssion" INDA Journal vol. 5, No. 2, pp. 22–26.

Van A. Wente "Superfine Themoplastic Fibers" Industrial Engineering Chemistry, Aug., 1956, vol. 48, No. 8, pp. 1342–1346.

Database WPI, Section Ch, Derwent Pub. Ltd., London, GB; Class A17, AN 74–00806V, XP002043546 & JP 48 060774 A (Sekisui Chem Co Ltd) see abstract.

Database WPI, Section Ch, Week 8948, Derwent Pub. Ltd., London, GB; Class A18, AN 89–353803, XP002043547 & JP 01 266 150 A (Showa Electric Wire Co Ltd) see abstract.

*Primary Examiner*—Jan H. Silbaugh
*Assistant Examiner*—Mark Eashoo
(74) *Attorney, Agent, or Firm*—Thomason, Moser & patterson, L.L.P.

(57) ABSTRACT

A process for rendering films, film composites, and articles made therefrom less resistant to passage of water vapor by passing a filled precursor film or film composite through the nip of interdigitating grooved rollers. The films or film composites are generally formed using a precursor film of a film forming polyolefin or polyolefin blend, with a relatively high filler loading and optionally an elastomer. A process is disclosed for making diapers or other disposable items where a relatively high water vapor is coupled with a resistance to liquid strikethrough. In one embodiment of the invention, the interdigitating grooved rollers are maintained in a temperature range of from about 91° F. to about 159° F.

18 Claims, 2 Drawing Sheets

U.S. PATENT DOCUMENTS

| | | | |
|---|---|---|---|
| 3,407,253 | 10/1968 | Yoshimura et al. | 264/289 |
| 3,424,649 | 1/1969 | Nyberg et al. | 161/253 |
| 3,426,754 | 2/1969 | Bierebaum et al. | 128/156 |
| 3,562,356 | 2/1971 | Nyberg et al. | 260/876 |
| 3,642,967 | 2/1972 | Doll | 264/51 |
| 3,654,929 | 4/1972 | Nilsson et al. | 128/287 |
| 3,678,134 | 7/1972 | Middlebrook | 260/876 |
| 3,683,917 | 8/1972 | Comeford | 128/287 |
| 3,832,267 | 8/1974 | Liu | 161/116 |
| 3,837,773 | 9/1974 | Raley | 264/173 |
| 3,840,418 | 10/1974 | Sabee | 156/244 |
| 3,844,865 | 10/1974 | Elton et al. | 156/229 |
| 3,870,593 | 3/1975 | Elton et al. | 161/159 |
| 3,894,827 | 7/1975 | Riley et al. | 425/363 |
| 3,903,234 | 9/1975 | Ikeda et al. | 264/210 R |
| 3,927,144 | 12/1975 | Hayashi et al. | 260/888 |
| 3,941,859 | 3/1976 | Batiuk et al. | 260/897 B |
| 3,969,562 | 7/1976 | Suzuki | 428/155 |
| 4,076,698 | 2/1978 | Anderson et al. | 526/348 |
| 4,091,164 | 5/1978 | Schwarz | 428/404 |
| 4,107,238 | 8/1978 | Roper et al. | 260/880 |
| 4,116,892 | 9/1978 | Schwarz | 521/62 |
| 4,116,914 | 9/1978 | Coran et al. | 260/30.6 R |
| 4,131,654 | 12/1978 | Herman et al. | 260/897 B |
| 4,132,698 | 1/1979 | Gessler et al. | 260/33.6 AQ |
| 4,134,951 | 1/1979 | Dow et al. | 264/147 |
| 4,135,023 | 1/1979 | Lloyd et al. | 428/167 |
| 4,144,008 | 3/1979 | Schwarz | 425/66 |
| 4,151,137 | 4/1979 | Duvdevani et al. | 260/23.5 |
| 4,153,664 | 5/1979 | Sabee | 264/289 |
| 4,153,751 | 5/1979 | Schwarz | 428/304 |
| 4,171,411 | 10/1979 | Ehrenfreund | 521/98 |
| 4,173,612 | 11/1979 | Kelly | 264/176 R |
| 4,205,021 | 5/1980 | Morita et al. | 525/240 |
| 4,210,709 | 7/1980 | Doi et al. | 429/250 |
| 4,211,808 | 7/1980 | Trankle | 428/131 |
| 4,212,787 | 7/1980 | Matsuda et al. | 260/33.6 AQ |
| 4,220,579 | 9/1980 | Rinehart | 260/33.6 AQ |
| 4,220,879 | 9/1980 | Hoshimi et al. | 310/68 R |
| 4,223,059 | 9/1980 | Schwarz | 428/198 |
| 4,226,952 | 10/1980 | Halasa et al. | 525/192 |
| 4,243,576 | 1/1981 | Fischer et al. | 260/42.15 |
| 4,251,585 | 2/1981 | Schwarz | 428/188 |
| 4,252,914 | 2/1981 | Halasa et al. | 525/98 |
| 4,253,461 | 3/1981 | Strickland et al. | 128/287 |
| 4,277,578 | 7/1981 | Yoshimura et al. | 525/211 |
| 4,285,100 | 8/1981 | Schwarz | 19/161.1 |
| 4,289,832 | 9/1981 | Schwarz | 428/542 |
| 4,298,647 | 11/1981 | Cancio et al. | 428/167 |
| 4,303,571 | 12/1981 | Jansen et al. | 260/33.6 AQ |
| 4,303,712 | 12/1981 | Woodroof | 428/58 |
| 4,303,714 | 12/1981 | Mercer | 428/135 |
| 4,315,882 | 2/1982 | Hiratsuka et al. | 264/171 |
| 4,316,828 | 2/1982 | Makowski et al. | 260/23.5 |
| 4,317,792 | 3/1982 | Raley et al. | 264/504 |
| 4,318,408 | 3/1982 | Korpman | 128/287 |
| 4,319,950 | 3/1982 | Sznopek et al. | 156/475 |
| 4,329,309 | 5/1982 | Kelly | 264/167 |
| 4,331,622 | 5/1982 | Doi et al. | 264/45.3 |
| 4,335,193 | 6/1982 | Doi et al. | 429/251 |
| 4,335,225 | 6/1982 | Collette et al. | 525/240 |
| 4,344,999 | 8/1982 | Gohlke | 428/212 |
| 4,350,655 | 9/1982 | Hoge | 264/145 |
| 4,351,784 | 9/1982 | Thomas et al. | 264/22 |
| 4,352,355 | 10/1982 | Mesek et al. | 128/287 |
| 4,353,945 | 10/1982 | Sampson | 428/90 |
| 4,357,439 | 11/1982 | Blumel et al. | 524/493 |
| 4,367,316 | 1/1983 | Tanaka et al. | 525/173 |
| 4,368,565 | 1/1983 | Schwarz | 26/99 |
| 4,369,284 | 1/1983 | Chen | 524/476 |
| 4,378,067 | 3/1983 | Butler et al. | 206/447 |
| 4,380,564 | 4/1983 | Cancio et al. | 428/167 |
| 4,381,364 | 4/1983 | Georgacopoulos et al. | 524/373 |
| 4,385,142 | 5/1983 | Bohm et al. | 524/68 |
| 4,402,688 | 9/1983 | Julemont | 604/385 |
| 4,418,112 | 11/1983 | Toyoda et al. | 428/212 |
| 4,425,127 | 1/1984 | Suzuki et al. | 604/366 |
| 4,425,129 | 1/1984 | Karami | 604/385 |
| 4,427,737 | 1/1984 | Cilento et al. | 428/315.7 |
| 4,435,141 | 3/1984 | Weisner et al. | 425/131.1 |
| 4,436,520 | 3/1984 | Lipko et al. | 604/385 |
| 4,438,167 | 3/1984 | Schwarz | 428/138 |
| 4,440,911 | 4/1984 | Inoue et al. | 525/301 |
| 4,446,189 | 5/1984 | Romanek | 428/152 |
| 4,449,977 | 5/1984 | Korpman | 604/366 |
| 4,450,026 | 5/1984 | Pieniak et al. | 156/164 |
| 4,460,646 | 7/1984 | Inoue et al. | 428/344 |
| 4,463,156 | 7/1984 | McGary, Jr. et al. | 528/65 |
| 4,465,729 | 8/1984 | Cancio et al. | 428/167 |
| 4,472,328 | 9/1984 | Sugimoto et al. | 264/41 |
| 4,476,150 | 10/1984 | Rose | 427/10 |
| 4,476,180 | 10/1984 | Wnuk | 428/220 |
| 4,479,989 | 10/1984 | Mahal | 428/35 |
| 4,480,061 | 10/1984 | Coughlin et al. | 524/13 |
| 4,485,133 | 11/1984 | Ohtsuka et al. | 428/35 |
| 4,517,714 | 5/1985 | Sneed et al. | 28/103 |
| 4,525,531 | 6/1985 | Zukosky et al. | 525/92 |
| 4,527,989 | 7/1985 | Karami | 604/385 |
| 4,534,769 | 8/1985 | De Jonckheere et al. | 604/369 |
| 4,535,020 | 8/1985 | Thomas et al. | 428/131 |
| 4,544,734 | 10/1985 | McCready | 528/288 |
| 4,556,688 | 12/1985 | McCready et al. | 525/33 |
| 4,556,705 | 12/1985 | McCready | 528/289 |
| 4,585,447 | 4/1986 | Karami | 604/385 |
| 4,585,604 | 4/1986 | Okuyama et al. | 264/41 |
| 4,590,020 | 5/1986 | Itaba et al. | 264/22 |
| 4,590,202 | 5/1986 | Remy | 514/392 |
| 4,613,640 | 9/1986 | Deisler et al. | 524/264 |
| 4,626,252 | 12/1986 | Nishizawa et al. | 604/370 |
| 4,627,993 | 12/1986 | Loomis | 428/36 |
| 4,628,073 | 12/1986 | Fisher | 525/70 |
| 4,636,340 | 1/1987 | Itaba et al. | 264/22 |
| 4,639,487 | 1/1987 | Hazelton et al. | 524/425 |
| 4,639,949 | 2/1987 | Ales et al. | 2/400 |
| 4,640,859 | 2/1987 | Hansen et al. | 428/105 |
| 4,657,539 | 4/1987 | Hasse | 604/385 |
| 4,663,220 | 5/1987 | Wisneski et al. | 428/221 |
| 4,673,619 | 6/1987 | Itaba et al. | 428/338 |
| 4,681,580 | 7/1987 | Reising et al. | 604/385 |
| 4,681,781 | 7/1987 | Murray et al. | 428/35 |
| 4,684,578 | 8/1987 | Inoue et al. | 428/462 |
| 4,704,112 | 11/1987 | Suzuki et al. | 604/378 |
| 4,704,238 | 11/1987 | Okuyama et al. | 264/41 |
| 4,705,812 | 11/1987 | Ito et al. | 521/92 |
| 4,713,068 | 12/1987 | Wang et al. | 604/366 |
| 4,713,069 | 12/1987 | Wang et al. | 604/378 |
| 4,714,735 | 12/1987 | Hodgson, Jr. et al. | 524/514 |
| 4,714,753 | 12/1987 | McCready et al. | 528/288 |
| 4,716,197 | 12/1987 | Seiss et al. | 525/75 |
| 4,719,144 | 1/1988 | Kamat | 428/257 |
| 4,721,592 | 1/1988 | Fruehauf et al. | 264/171 |
| 4,725,481 | 2/1988 | Ostapchenko | 428/213 |
| 4,732,947 | 3/1988 | McCready et al. | 525/437 |
| 4,734,324 | 3/1988 | Hill | 428/317.3 |
| 4,740,258 | 4/1988 | Breitscheidel | 156/209 |
| 4,740,564 | 4/1988 | McCready et al. | 525/437 |
| 4,740,565 | 4/1988 | McCready et al. | 525/437 |
| 4,758,297 | 7/1988 | Calligarich | 156/251 |
| 4,775,375 | 10/1988 | Aledo | 604/378 |
| 4,777,073 | 10/1988 | Sheth | 428/155 |
| 4,791,144 | 12/1988 | Nagou et al. | 521/90 |

| | | | |
|---|---|---|---|
| 4,793,956 | 12/1988 | Nogiwa et al. | 264/41 |
| 4,795,790 | 1/1989 | McCready et al. | 525/437 |
| 4,798,604 | 1/1989 | Carter | 604/383 |
| 4,798,858 | 1/1989 | McCready et al. | 524/100 |
| 4,803,244 | 2/1989 | Umpleby | 525/105 |
| 4,806,300 | 2/1989 | Walton et al. | 264/288.8 |
| 4,808,252 | 2/1989 | Lash | 156/73.1 |
| 4,814,124 | 3/1989 | Aoyama et al. | 264/41 |
| 4,814,380 | 3/1989 | Liu | 525/66 |
| 4,814,396 | 3/1989 | Liu | 525/433 |
| 4,820,590 | 4/1989 | Hodgson et al. | 428/516 |
| 4,824,718 | 4/1989 | Hwang | 428/284 |
| 4,829,124 | 5/1989 | Clark | 525/108 |
| 4,833,172 | 5/1989 | Schwarz et al. | 521/62 |
| 4,848,564 | 7/1989 | Scheller et al. | 206/83.5 |
| 4,877,679 | 10/1989 | Leatherman et al. | 428/224 |
| 4,878,974 | 11/1989 | Kagawa | 156/85 |
| 4,879,078 | 11/1989 | Antoon, Jr. | 264/41 |
| 4,892,901 | 1/1990 | Liu | 524/303 |
| 4,902,553 | 2/1990 | Hwang et al. | 428/156 |
| 4,910,245 | 3/1990 | Flynn et al. | 524/298 |
| 4,921,653 | 5/1990 | Aoyama et al. | 264/41 |
| 4,921,749 | 5/1990 | Bossaert et al. | 428/216 |
| 4,929,303 | 5/1990 | Sheth | 156/209 |
| 4,935,287 | 6/1990 | Johnson et al. | 428/198 |
| 4,957,943 | 9/1990 | McAllister et al. | 521/64 |
| 4,970,259 | 11/1990 | Mitchell et al. | 428/220 |
| 4,977,014 | 12/1990 | Mitchell et al. | 524/505 |
| 4,978,570 | 12/1990 | Heyn et al. | 428/231 |
| 4,992,505 | 2/1991 | Liu | 524/416 |
| 4,995,930 | 2/1991 | Merz et al. | 156/209 |
| 5,008,204 | 4/1991 | Stehling | 436/85 |
| 5,008,296 | 4/1991 | Antoon, Jr. et al. | 521/91 |
| 5,017,323 | 5/1991 | Balk | 264/288.4 |
| 5,021,475 | 6/1991 | Isayev | 524/30 |
| 5,026,798 | 6/1991 | Canich | 526/127 |
| 5,032,450 | 7/1991 | Rechlicz et al. | 428/196 |
| 5,034,078 | 7/1991 | Hodgson, Jr. et al. | 156/85 |
| 5,035,338 | 7/1991 | Kaufhold et al. | 213/50 |
| 5,047,495 | 9/1991 | Kolycheck | 528/76 |
| 5,055,338 | 10/1991 | Sheth | 428/155 |
| 5,066,526 | 11/1991 | German, Jr. | 428/35.2 |
| 5,068,138 | 11/1991 | Mitchell et al. | 428/36.8 |
| 5,098,755 | 3/1992 | Tanquary et al. | 428/35.5 |
| 5,145,747 | 9/1992 | Jottier | 428/484 |
| 5,167,652 | 12/1992 | Mueller | 604/385.1 |
| 5,169,712 | 12/1992 | Tapp | 428/315.5 |
| 5,174,231 | 12/1992 | White | 112/420 |
| 5,182,069 | 1/1993 | Wick | 264/210.2 |
| 5,198,401 | 3/1993 | Turner et al. | 502/155 |
| 5,206,075 | 4/1993 | Hodgson, Jr. | 428/216 |
| 5,241,031 | 8/1993 | Mehta | 526/348.1 |
| 5,272,236 | 12/1993 | Lai et al. | 526/348.5 |
| 5,278,272 | 1/1994 | Lai et al. | 526/348.5 |
| 5,296,184 | 3/1994 | Wu et al. | 264/154 |
| 5,317,035 | 5/1994 | Jacoby et al. | 521/143 |
| 5,322,728 | 6/1994 | Davey et al. | 428/296 |
| 5,358,792 | 10/1994 | Mehta et al. | 428/516 |
| 5,364,695 | 11/1994 | Gurevitz | 428/323 |
| 5,376,439 | 12/1994 | Hodgson et al. | 428/220 |
| 5,382,461 | 1/1995 | Wu | 428/86 |
| 5,382,630 | 1/1995 | Stehling et al. | 525/240 |
| 5,385,769 | 1/1995 | Wick | 428/141 |
| 5,399,396 | 3/1995 | Ohlsson et al. | 428/34.7 |
| 5,409,761 | 4/1995 | Langley | 428/198 |
| 5,415,905 | 5/1995 | Middlesworth et al. | 528/35.7 |
| 5,445,862 | 8/1995 | Kaneko et al. | 428/148 |
| 5,447,788 | 9/1995 | Rhim et al. | 428/284 |
| 5,451,450 | 9/1995 | Erderly et al. | 429/220 |
| 5,470,811 | 11/1995 | Jejelowo et al. | 502/117 |
| 5,472,775 | 12/1995 | Obijeski et al. | 428/220 |
| 5,500,260 | 3/1996 | Halle et al. | 428/35.7 |
| 5,500,360 | 3/1996 | Ahlquist et al. | 435/172.3 |
| 5,525,659 | 6/1996 | Falla et al. | 524/257 |
| 5,549,777 | 8/1996 | Langdon et al. | 156/244.18 |
| 5,558,930 | 9/1996 | DiPoto | 428/216 |
| 5,560,974 | 10/1996 | Langley | 428/198 |
| 5,565,250 | 10/1996 | Ohlsson et al. | 428/34.7 |
| 5,571,619 | 11/1996 | McAlpin et al. | 428/364 |
| 5,575,785 | 11/1996 | Gryskiewicz et al. | 604/385.2 |
| 5,580,910 | 12/1996 | Isaac et al. | 529/17 |
| 5,580,914 | 12/1996 | Falla et al. | 524/257 |
| 5,674,944 | 10/1997 | Falla et al. | 525/239 |
| 5,690,949 | 11/1997 | Weimer et al. | 424/402 |
| 5,695,868 | 12/1997 | McCormack | 428/283 |
| 5,695,871 | 12/1997 | Tallentire et al. | 428/320.2 |
| 5,738,111 | 4/1998 | Weimer et al. | 128/849 |
| 5,783,270 | 7/1998 | Fischer et al. | 428/35.2 |
| 5,814,569 | 9/1998 | Suzuki et al. | 442/328 |
| 5,865,926 * | 2/1999 | Wu et al. | 156/229 |
| 5,910,225 | 6/1999 | McAmish et al. | 156/229 |
| 5,995,187 | 9/1999 | McCormack et al. | 428/315.5 |
| B1 3,860,003 | 4/1989 | Buell | 604/385.2 |

FOREIGN PATENT DOCUMENTS

| | | |
|---|---|---|
| 2130192 | 2/1998 | (CA). |
| 2 035 117 | 1/1971 | (DE). |
| 34 36 065 A1 | 4/1986 | (DE). |
| 43 11 422 A1 | 10/1994 | (DE). |
| 38 50 987 T2 | 12/1994 | (DE). |
| 32 33 693 C2 | 1/1995 | (DE). |
| 0 032 804 A2 | 7/1981 | (EP). |
| 0 114 964 A1 | 8/1984 | (EP). |
| 0 119 815 A2 | 9/1984 | (EP). |
| 0 119 827 A2 | 9/1984 | (EP). |
| 0 193 938 A2 | 9/1986 | (EP). |
| 0 114 964 B1 | 11/1986 | (EP). |
| 0 201 331 A2 | 11/1986 | (EP). |
| 0 219 198 A1 | 4/1987 | (EP). |
| 0 227 037 | 7/1987 | (EP). |
| 0 227 037 A2 | 7/1987 | (EP). |
| 0 232 060 A3 | 8/1987 | (EP). |
| 0 119 827 B1 | 7/1988 | (EP). |
| 0 276 100 A1 | 7/1988 | (EP). |
| 0 283 200 A2 | 9/1988 | (EP). |
| 0 283 200 A3 | 9/1988 | (EP). |
| 0 283 200 B1 | 9/1988 | (EP). |
| 0 288 021 | 10/1988 | (EP). |
| 0 288 021 A2 | 10/1988 | (EP). |
| 0 288 021 A3 | 10/1988 | (EP). |
| 0 201 331 B1 | 12/1989 | (EP). |
| 0 352 802 | 1/1990 | (EP). |
| 0 352 802 A2 | 1/1990 | (EP). |
| 0 361 865 A2 | 4/1990 | (EP). |
| 0 361 865 A3 | 4/1990 | (EP). |
| 0 361 865 B1 | 4/1990 | (EP). |
| 0 193 938 B1 | 6/1990 | (EP). |
| 0 385 599 A2 | 9/1990 | (EP). |
| 0 385 599 A3 | 9/1990 | (EP). |
| 0 219 198 B1 | 10/1991 | (EP). |
| 0 550 115 A2 | 7/1993 | (EP). |
| 0 550 115 A3 | 7/1993 | (EP). |
| 0 598 970 | 1/1994 | (EP). |
| 0 598 970 A1 | 6/1994 | (EP). |
| 0 691 203 A1 | 1/1996 | (EP). |
| 0 742 248 A1 | 11/1996 | (EP). |
| 0 629 151 B1 | 12/1996 | (EP). |
| 0 662 988 B1 | 2/1997 | (EP). |
| 0 769 525 A1 | 4/1997 | (EP). |
| 0 682 678 B1 | 12/1998 | (EP). |
| 0 604 731 B1 | 6/1999 | (EP). |
| 2.074.338 | 9/1971 | (FR). |

| | | | | | | |
|---|---|---|---|---|---|---|
| 2.446.176 | 8/1980 | (FR) . | | 2-179543 | 7/1990 | (JP) . |
| 1 454 218 | 11/1976 | (GB) . | | 3-221540 | 9/1991 | (JP) . |
| 2 101 468 | 1/1983 | (GB) . | | 6-29842 | 2/1994 | (JP) . |
| 2115702 | 9/1983 | (GB) . | | 7-116429 | 5/1995 | (JP) . |
| 2 137 632 | 10/1984 | (GB) . | | 7-118431 | 5/1995 | (JP) . |
| 2 178 433 | 2/1987 | (GB) . | | 175038 B1 | 2/1994 | (PL) . |
| 2151538 | 7/1995 | (GB) . | | 93/03093 | 2/1993 | (WO) . |
| 2285408 | 7/1995 | (GB) . | | 93/16863 | 9/1993 | (WO) . |
| 2290052 | 12/1995 | (GB) . | | 94/01276 | 1/1994 | (WO) . |
| 48-60774 | 8/1973 | (JP) . | | 94/01376 | 1/1994 | (WO) . |
| 51-30856 | 3/1976 | (JP) . | | 94/06857 | 3/1994 | (WO) . |
| 54-120646 | 9/1979 | (JP) . | | 94/18263 | 8/1994 | (WO) . |
| 54-120658 | 9/1979 | (JP) . | | 95/02630 | 1/1995 | (WO) . |
| 55-110141 | 8/1980 | (JP) . | | 95/03765 | 2/1995 | (WO) . |
| 57-02350 | 1/1982 | (JP) . | | 95/07314 | 3/1995 | (WO) . |
| 57-117038 | 7/1982 | (JP) . | | 95/09199 | 4/1995 | (WO) . |
| 57-117039 | 7/1982 | (JP) . | | 95/16562 | 6/1995 | (WO) . |
| 58-129034 | 8/1983 | (JP) . | | WO 95/03765 | 9/1995 | (WO) . |
| 61-9448 | 1/1986 | (JP) . | | 96/19346 | 6/1996 | (WO) . |
| 61-284439 | 12/1986 | (JP) . | | 96/39032 | 12/1996 | (WO) . |
| 62-169642 | 7/1987 | (JP) . | | 98/04397 | 2/1998 | (WO) . |
| 62-176843 | 8/1987 | (JP) . | | 98/05502 | 2/1998 | (WO) . |
| 62-179543 | 8/1987 | (JP) . | | 98/24834 | 6/1998 | (WO) . |
| 62-282003 | 12/1987 | (JP) . | | 98/29247 | 7/1998 | (WO) . |
| 64-49619 | 2/1989 | (JP) . | | 98/29481 | 7/1998 | (WO) . |
| 64-79620 | 3/1989 | (JP) . | | 98/29504 | 7/1998 | (WO) . |
| 2-276636 | 4/1989 | (JP) . | | WO 98/29504 | 9/1998 | (WO) . |
| 1-144431 | 6/1989 | (JP) . | | 98/58799 | 12/1998 | (WO) . |
| 1-235439 | 9/1989 | (JP) . | | 99/23139 | 5/1999 | (WO) . |
| 1-264031 | 10/1989 | (JP) . | | | | |
| 1-266150 | 10/1989 | (JP) . | | | | |
| 2-36938 | 2/1990 | (JP) . | | | | |

\* cited by examiner

PROCESS FOR ADJUSTING WVTR AND OTHER PROPERTIES OF A POLYOLEFIN FILM

RELATED APPLICATIONS

This application is a continuation-in-part application of co-pending U.S. Application No. 08/690,136 filed Jul. 31, 1996. This application claims the benefit of U.S. Provisional Application Nos. 60/104,452 filed Oct. 16, 1998 and 60/104,455 filed Oct. 16, 1998 and U.S. Provisional Application Nos. 60/104,948 filed Oct. 20, 1998 and 60/104,985 filed Oct. 20, 1998.

TECHNICAL FIELD

This invention relates generally a process of adjusting the water vapor transmission/porosity of films and film composites, while maintaining general resistance to liquid transmission (strikethrough). More specifically this invention is directed towards a process for producing films, film composites, and articles made therefrom, that are made permeable to water vapor, by passing them through interdigitating grooved rollers. Also, more specifically this invention is directed toward filled polypropylene films having excellent Water Vapor Transmission Rates (WVTR), high tear strength, high dart impact strength, and a soft feel.

BACKGROUND OF THE INVENTION

Polyolefin films which are rendered more permeable to water vapor using filler loading and orientation are known.

Such films or film composites are said to be more breathable, that is to have improved, increased permeability to water vapors, while maintaining a resistance to liquid strikethrough (defined herein). Uses of such films or film composites include on a diaper the permeability of which may permit the passage of moisture vapor and air, while substantially preventing the passage of liquid. The advantages of such a film used in a diaper are that after the wearer voids, the liquid is generally retained, while much of the liquid vapor can escape decreasing the "wet feeling", and lowering the possibility of uncomfortable diaper rash.

Interdigitating grooved rollers have been used to orient either certain films or exclusively nonwoven laminates. Use of such rollers to orient (i.e., stretch) a film or nonwoven substrate is typically referred to as a ring-rolling process. To increase the water vapor transmission rate ("WVTR") of a film stretched by a ring-rolling process, it has been customary to increase either the filler loading in the formulation or the depth of engagement of the interdigitating grooves. However, both of these processing options have technical limitations on their ability to increase the WVTR of a film. Also, each option can potentially have negative effects on the physical properties of the stretched film, if a specific film's tolerance for filler loading and/or groove engagement depth is exceeded. Accordingly, there is a need for alternative means for increasing the WVTR, without negatively effecting a film's physical properties.

Also, it is desired for many applications of breathable films, such as disposable diapers, adult incontinent products, and feminine hygiene devices, to produce a film appearance that can provide the manufacturer and consumers of such products visual evidence of those products made of breathable films versus those made from non-breathable films.

U.S. Pat. No. 4,472,328, assigned to Mitsubishi Chemical Industries, Ltd., suggests a breathable polyolefin film prepared from a polyolefin/filler composition having from 20 percent to 80 percent by weight of a filler such as a surface treated calcium carbonate. A liquid or waxy hydrocarbon polymer elastomer such as a hydroxyl-terminated liquid polybutadiene was purported to produce a precursor film that could be mono-axially or biaxially stretched to make a film breathable. The breathable film described by Mitsubishi is also described in Great Britain Patent No.2,115,702, assigned to Kao Corporation. The Kao patent fuirther describes a disposable diaper prepared with a breathable film as disclosed by the Mitsubishi patent. The breathable film is used as a backing for the diaper to contain liquid.

U.S Pat. No. 4,350,655 by W. H. Hoge, assigned to Biax Fiber Film, describes a porous polyolefm synthetic paper film containing at least 50 percent by weight of a coated inorganic filler. The film composition was comprised of from 50 to 70 weight percent of an inorganic filler material coated with a silicon or titanium fatty acid ester. To produce such a film product, Hoge teaches to cool the disclosed film substrate down into a temperature range of 10° C. to 70° C. (i.e., 50° F. to 158° F. respectively) prior to stretching the film. Hoge refers to such a process as a "cold stretching " the film. Hoge also indicates that such cold stretching helps develop the desired void volume and surface ruptures per unit area so that weight percent resin content of the final product ranges from 0.18 to about 0.32 g/cm$^3$. Moreover, the precursor film is formed without the addition of an elastomer and contains an inorganic filler surface coated with either a Si or Ti fatty acid ester. Some of the resulting films were stated to be both vapor and liquid permeable, however, at least one film (Example 3) was stated to be permeable to air.

U.S. Pat. No. 4,777,073 (Sheth) suggests a breathable film produced by stretching of a precursor film prepared from a polyolefin/filler composition. Sheth suggests that the permeability and strength, especially tear strength are improved by melt embossing the precursor film with a patterned melt embossing roller and stretching the film to impart a pattern of different film thickness having greater permeability within the areas of reduced thickness compared to the areas of greater thickness.

Most of these techniques require that a film or film composite be rendered breathable, regardless of the technique but generally through tentering (for transverse direction or TD orientation, and differential speeds of two rollers for machine direction or MD orientation), in a separate operation, prior to final construction of the end-use article, for instance the diaper, leading to expensive double processing or more expensive transport of the film rendered less dense by the tentering operation.

Among the most serious limitations, is the extreme difficulty in producing a cost effective lamination between polypropylene nonwoven materials and polyethylene breathable films. Traditional glue, hotmelt, or meltblown adhesive techniques can be used, but require the additional cost and process complexity of the gluing system and the adhesive. The preferred method of heat lamination was generally not reliable because the difference in melting points of the polypropylene nonwoven (~161° C.) and the polyethylene film (~125° C.). To achieve an adequate lamination bond strength between the two materials, pin holes or damage to the breathable film at the film/nonwoven bond site resulted.

Previous polypropylene breathable films, while having lamination advantages over polyethylene films, have been deficient in a number of other performance categories. Film oriented by traditional Machine Direction Orientation, Transverse Direction Orientation, or Biaxial Orientation (all known in the art) have had very low tear and impact strength.

For those product applications which do not laminate the breathable film directly to a nonwoven, or which by nature of the product a hot melt type adhesive gluing system is desirable (such as a breathable film diaper backsheet), polypropylene breathable film will be more resistant to glue burn through of the film. Thus, the use of a polypropylene breathable film helps to achieve product integrity. Also, the use of higher temperature glues, as well as a lower quantity of glue is required for adequate product bond strength.

Accordingly, there is need for an improved ring-rolling process and/or polymer film composition that can increase the WVTR of a film, without significantly diminishing the film's physical properties. There is also a commercial need for a polypropylene microporous breathable film with high tear and impact strengths well as a soft feel. Also, there is need for films produced by such an improved process to be readily distinguishable as breathable films.

SUMMARY OF THE INVENTION

According to one aspect of the present invention, there is provided a process for producing a film having a WVTR greater than 200 g/m$^2$/day at 38° C. and 90% relative humidity comprising a polyolefin and a filler, said process comprising: a) extruding a precursor film from said polyolefin blend comprising said first and said second polymer compositions and said filler, said filler concentration being in a range of from about 16.5 to about 71.5 wt.%; and b) passing said precursor film between at least one pair of interdigitating grooved rollers, said rollers being maintained in a temperature range from about 91° F. to about 159° F., so that said film is heated to produce said film having a WVTR greater than 200 g/m$^2$/day at 38° C. and 90% relative humidity.

According to another aspect of the present invention, there is provided a process for producing a film having a WVTR of at least 200 g/m$^2$/day at 38° C. and 90% relative humidity comprising a polyolefin blend, said polyolefin blend having at least a first and a second polymer composition, and a filler, said process comprising: a) extruding a precursor film from said polyolefin blend comprising said first and said second polymer compositions and said filler, said filler concentration being in a range of from about 16.5 to about 71.5 wt.%, wherein, i) said first polymer composition is a polypropylene and ii) said second polymer composition is selected from the group consisting of elastomers, plastomers, styrenic block copolymers, ethylene-maleic anhydride copolymers, ethylene ethyl acetate, and combinations thereof; and b) passing said precursor film between at least one pair of interdigitating grooved rollers so that said film has at least: i) a WVTR in a range of from about 200 g/m$^2$/day to about 10,000 g/m$^2$/day at 38° C. and 90% relative humidity, ii) a dart drop impact in a range of from about 100 grams to about 300 grams, and iii) an elongation selected from the group consisting of machine direction, transverse direction and combinations thereof in a range of from about 150% to about 550%.

BRIEF DESCRIPTION OF THE DRAWINGS

The foregoing aspects, features and advantages of the present invention will become clearer and more fully understood when the following detailed description, and appended claims are read in conjunction with the accompanying drawings, in which is a schematic drawing of an embodiment of our invention for imparting breathability to a film or film composite:

DETAILED DESCRIPTION OF PREFERRED EMBODIMENTS

Figure 1:
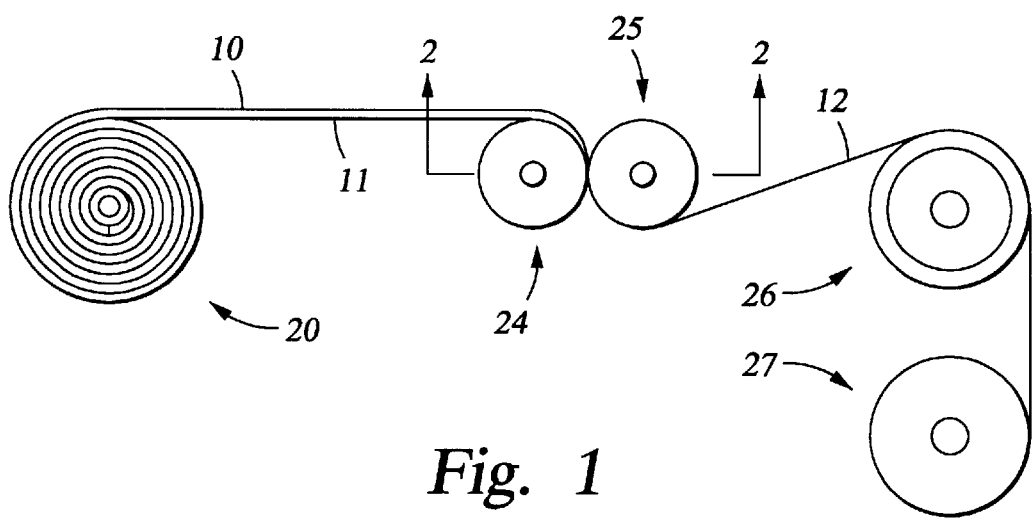
FIG. 1 is a schematic view of a process for converting a precursor film (and optionally other layers) into a film with greater WVTR.

We have discovered that certain polyolefin films and film composites can be processed to have greater water vapor transmission rates, relatively low liquid strikethrough, while maintaining film integrity, by using certain film forming formulations and techniques and passing the film, the film composite and/or the finished fabricated disposable article, through a nip of at least one pair of interdigitating grooved rollers.

We have discovered that applying heat to interdigitating grooved rollers results in a substantial improvement in orientation effectiveness (WVTR increases), and imparts a 3 dimensionality to the film which differentiates it from other breathable film. In addition a new control is provided for the adjustment of film breathability, i.e. rather than require a formulation change, or adjustment to the depth of activation, to control WVTR levels, roller temperature merely needs to be adjusted. As can be seen from the following examples, with all other factors constant, an increase in interdigitating roll temperature from 70° F. to 140° F., increases WVTR from 1900 g/m$^2$/day to 4100 g/m$^2$/day.

We have also discovered that producing a precursor film from a polypropylene and filler (preferably calcium carbonate) blend, then incrementally orienting the film with interdigitating grooved rollers in the machine direction, or the transverse direction, or both, will yield a reasonably soft film (to the touch) with good impact and tear strength. It was further discovered that by adding a minority amount of low density polyethylene, extrusion processability was greatly improved. It was further discovered that the addition of a minority amount of an elastomer or plastomer improved impact and tear strength further, and contributed to an even softer film "feel". Impact strength is approximately double that of previously available polypropylene breathable films stretched by conventional techniques, other than interdigitating grooved rollers. MD tear strength is more than triple that of Machine Direction Oriented and Biaxial Oriented polypropylene breathable films. TD tear strength is greater than triple that of Transverse Direction Oriented and Biaxial Oriented polypropylene breathable films. Because stretching such film blends by interdigitating grooved rollers was expected to produce film with substantially similar physical properties as films with stretched with conventional stretching techniques, such dramatic improvements in physical properties proved most surprising.

In certain embodiments of the invention, a polyolefin film or film composite comprises at least one layer of a disposable article and is rendered breathable by passing the film, film composite or fabricated article through interdigitating grooved rollers. The film, film composite or fabricated article will have either a single layer or multilayer construction and the polyolefin/filler combination can be co-extruded, laminated or blended with other polymers or polymer based fabricated articles.

In an embodiment of the invention, a film ("precursor film") is made, utilizing a polyolefrn or a polyolefin blend with a relatively higher filler loading, generally including embossing a pattern thereupon, such that its subsequent manipulation, either by itself, in a film composite or as a part of a disposable article, will render the film breathable (hereinafter defined as water vapor permeable, within certain limits of WVTR, while maintaining a certain level of liquid impermeability) while maintaining a minimum level of physical properties, elongation/tensile strength being of most importance. The manipulation of the film, film composite, and/or fabricated disposable article includes passing all or parts of the film, film composite, and/or fabricated disposable article through a grooved roller and/or interdigitating grooved rollers, at a rate sufficient to develop a minimum level of breathability to the film or film portion of the article, at a commercial and economical rate.

The tear strength, elasticity, and softness of a film prepared from the polyolefin/filler composition may be improved by addition of small amounts of an olefinic elastomer.

The WVTR desired is above 100 g/m$^2$/day @ 38° C., 90% RH (Relative Humidity), preferably above 200 g/m$^2$/day, and can be easily greater than 1000 g/m$^2$/day.

INTRODUCTION

This invention concerns all polyolefin/filler based breathable films that have high WVTR, the ability to be drawn down to low basis weights, and methods for making same. Particularly useful in these films and methods are impact copolymer polypropylene. The process is also effective for all polyolefin materials. The term impact copolymer herein refers to a homopolymer matrix having a small amount of an ethylene/propylene copolymer dispersed throughout.

This invention further includes certain polyolefins, their conversion into fabricated articles such as films, articles made from such films, and applications in which such articles having high WVTR combined with good physical properties are desirable. The resulting films, and film composites, (including co-extruded and laminated films) have combinations of properties rendering them superior and unique to films or film composites previously available. The films disclosed herein are particularly well suited for use in producing certain classes of high WVTR films, consumer and industrial articles using the films in combination with for instance, polymeric woven or non-woven materials. Such consumer articles include, but are not limited to diapers, adult incontinence devices, feminine hygiene articles, medical and surgical gowns, medical drapes, industrial apparel, building products such as "house-wrap", roofing components, and the like made using one or more of the films disclosed herein. Additionally the films of the present invention may also be used in metallized films with a high WVTR, according to the disclosure of U.S. Pat. No. 5,055, 338, fully incorporated herein for purposes of U.S. patent practice.

High WVTR films, high WVTR film composites, and disposable articles made therefrom of our invention, are produced from a precursor film that is prepared from a polymer composition that comprises at least one polyolefin component, at least one filler component, and optionally an elastomeric component. The polyolefin component may be any polyolefin which is suitable for film formation such as homo- or co-polymer polypropylene, home or co-polymer polyethylenes or blends thereof. A preferred polyolefin is a copolymer of propylene and low density polyethylene, particularly preferred is linear low density polyethylene. The linear low density polyethylene may be a polymer made from either traditional Ziegler-Natta or metallocene catalysts, or combinations thereof.

In an embodiment of the invention, the films, film composites, and articles made therefrom based on polyolefin filler combinations, when passed through a nip of interdigitating grooved rollers (hereinafter used interchangeably with "ring-rolling"would surprisingly and unexpectedly have improved water vapor transmission rates while maintaining resistance to liquid permeability; and retaining film integrity. Following is a detailed description of certain preferred films, film composites, and/or fabricated disposable articles made therefrom, within the scope of the present invention. Also disclosed are preferred methods of producing these films, film composites, and fabricated disposable articles made therefrom as well as preferred applications thereof. Those skilled in the art will appreciate that numerous modifications to these preferred embodiments can be made without departing from the scope of the invention. For example: though the properties of certain films, film composites, and fabricated articles such as diapers are exemplified, especially after ring-rolling, the films and composites will have numerous other uses. To the extent our description is specific, it is solely for the purpose of illustrating preferred embodiments of our invention and should not be taken as limiting the present invention to these specific embodiments.

It will be appreciated by those of ordinary skill in the art that the films and film composites of certain embodiments of the present invention, can be combined with other polymers or polymer based fabricated articles such as films, fibers, fabrics (including non-woven fabrics) and the like, depending on the intended function of the resulting film, film composite or fabricated article.

As an example of such combinations, by extrusion coating, co-extrusion coating, or by co-exrusion or laminating of the film with other polymer films, e.g. polyolefin, other properties may be achieved. For instance, after ring-rolling an entire film cross-section, certain (machine direction) sections could be extrusion coated to eliminate breathability in those selected portions so coated. Also contemplated are varying combinations of the precursor film, or the film after ring-rolling, with other films, or non-woven fabrics, generally made from one or more polyolefins. Such combinations, while including the precursor or the post ring-rolled film, can include several combinations, such as non-woven/film, film/non-woven, film/non-woven/film, film/film, and the like.

Other methods of improving WVTR of a film or article fabricated from the film, may be used in addition to use of the filled polyolefin and process of passing the filled polyolefin film through the nip of interdigitating grooved rollers described herein, without departing from the intended scope of the invention. For example, including microporous voids through pin-point punctures (also known as "apertured film") to improve the WVTR, in addition to ring-rolling is not excluded by the present invention. Also, it is well known that manipulation of a film by changing quench conditions during melt processing, and/or by irradiating the film will have an effect on WVTR and/or physical properties. Such mechanical or other treatment or manipulation is not excluded by this invention.

Films or film composites employing the polyolefin/filler blends of certain embodiments of the present invention can be oriented, annealed, or crosslinked Additionally, polyolefin/filler combinations of the present invention can be made into film by processes including blown or cast film manufacturing techniques. The blend components can function to modify barrier, opacity, sealing, cost, or other functions that will be known to those of ordinary skill in the art.

The films or composite structures are often used in infant diapers, toddler training pants, adult incontinence devices, medical drapes and apparel, such as surgical gowns, feminine hygiene articles, and the like. Use of the term "film composites" may include one or more film and/or non-woven layers bonded mechanically, thermally, or adhesively to the film. Such non-woven materials include spun-bond, meltblown, and combinations thereof.

Such non-woven materials are most often made from polyolefins, such as homopolymer polyethylene, copolymer polyethylene (including one or more of α-olefins of 4–10 carbon atoms, vinyl acetate, ethylenically unsaturated acrylic acid esters, acrylic acid, methacryclic acid, ionomers, polypropylene homopolymers, polypropylene copolymers including one or more of ethylene and α-olefins of 4–10carbon atoms, homopolymer and copolymer polypropylene).

Components of A Precursor Film

Film Forming Polyolefin

Most film forming polyolefins and combinations of film forming polyolefins may be used in embodiments of our invention.

Polyolefin Component

The polyolefm component can be any film forming polyolefin, including polyethylene and polypropylene and others, or polyolefin blend. Examples of suitable materials are listed in Table 1 below.

Generally the preferred α-olefins include those selected from the group consisting of butene-1, pentene-1, 4-methyl-1-pentene, hexene-1, octene-1, decene-1 and combinations thereof. Most preferred are ethylene copolymers of butene-1, hexene-1, octene-1 and combinations thereof. The comonomers may be present in amounts up to 20 mole percent. The amount of comonomer or comonomers will generally determine density, for instance HDPE will have from 0 to 1 mole percent comonomer, while plastomers with densities lower than 0.900 g/cm$^3$ will have up to 15 or even 20 mole percent comonomer(s). Such polyethylenes may be made utilizing traditional Ziegler-Natta, chromium based, and metallocene catalysts which may be used with alumoxane and/or ionic activators. Processes useful for preparing such polyethylenes include gas phase, slurry, solution and the like. The density of polyethylenes such as these, in preferred embodiments, will generally be in the range of from about 0.900 and 0.935 g/cm$^3$, preferably in the range of from about 0.910 to 0.925 g/cm$^3$, most preferably from about 0.915 to 0.920 g/cm$^3$. The polyethylenes will have a melt index in the range of from about 0.1 to about 10 g/10 min, preferably 0.5 to 5 g/10 min, generally consistent with film forming conditions.

Polypropylene

Polypropylene may be used in conjunction with one or more polyethylenes, or by-itself as the polyolefin component of the precursor film. Polypropylene may be made from many of the catalysts and processes discussed supra, including optional inclusion of one or more α-olefins. As indicated in Table 1, one of the preferred polymers is a random copolymer having low levels, for example up to about 8 wt.

TABLE 1

Suitable Polymers & Relative Benefits

| Polymer | Impact | Tear | Softness | Drawdown |
|---|---|---|---|---|
| Metallocene Homopolymers and Copolymers (e.g. Exxon Achieve ™ PD3854) | Preferred | Preferred | Preferred | Most Preferred |
| Random Copolymer PP (e.g. Exxon PP 9263) | More Preferred | More Preferred | More Preferred | More Preferred |
| Impact Copolymer polypropylene (e.g. Exxon PP 7623) | Most Preferred | Most Preferred | Most Preferred | Preferred |
| Homopolymer PP (e.g. Exxon PP 1016) | Preferred | Preferred | Preferred | Preferred |
| Exxon LD 3003 | Preferred | Preferred | Preferred | Preferred |
| Elastomer | Preferred | Preferred | Preferred | Preferred |
| Plastomer | Most Preferred | Most Preferred | Most Preferred | Most Preferred |

Polyethylene

Linear low density polyethylenes are among the materials favored in embodiments of the invention. Linear low density polyethylene (LLDPE), generally that having density from 0.910 to 0.935 g/cm$^3$ and a melt index from 0.01 to 10 dg/min. Another polyolefin that may be considered in such composites is very low density polyethylene (VLDPE, also plastomer) which will have densities in the range of from about 0.860 to about 0.910 g/cm$^3$.

Conventional high pressure low density polyethylene (LDPE) is another example of a suitable polyethylene which has a density of from 0.910 to 0.925 g/cm$^3$.

High density polyethylene (HDPE) having densities in the range of from about 0.935 to about 0.970 g/cm$^3$ may also be considered. Such polyethylenes may be produced by copolymerizing ethylene with one or more $C_4$ to $C_{20}$ α-olefin.

%, of ethylene randomly included in a predominantly polypropylene chain.

Elastomer

One or more elastomers may be included in the polyolefm component. Such elastomers include, but are not limited to vulcanized natural rubber, ethylene alpha olefin rubber (EPM), ethylene alpha olefin diene monomer rubber (EPDM), styrene-isoprene-styrene (SIS), styrene-butadiene-styrene (SBS), styrene-ethylene-butylene-styrene (SEBS), ethylene-propylene (EP), ethylene-vinyl acetate copolymer (EVA), ethylene-maleic anyhydride (EMA), ethylene-acrylic acid (EEA), butyl rubber and the like. Of these SIS and SBS are preferred, with SBS more particularly preferred. The range of elastomer inclusion are generally from about 1.4 to about 25 wt.%, preferably from about 1.4 to about 20 wt.%, and more preferably from about 1.4 to 17.2 wt.%.

Amounts of each component can vary with the desired properties for the precursor film or film composite. For instance, a nominal 0.917 g/cm³ density LLDPE may be combined with 4 wt.% of an elastomer. Such a combination might provide improved elastic behavior.

Other components in a film forming polyolefin are not excluded. Such components may include additives such as antioxidants, anti-static agents, colors and the like, well known to those of ordinary skill. Further, blending of polyolefins with polymers is also contemplated. For example, blending of traditional Ziegler Natta catalyzed (ZN), chromium catalyzed (CR), metallocene catalyzed (MCN) and free radical initiated (FR) polyolefins using one or all in a blend as the film forming component is contemplated. For instance including, but not limited to MCN/ZN, MCN/CR, MCN/FR, MCN/ZN/FR, combinations and the like are contemplated. Other free radical initiated polyethylenes, high pressure polyethylene, ethylene homopolymers as well as ethylene copolymers may be included.

Both in the case of other polyolefins and the elastomeric polymers, the combinations should be generally formable into a film.

As used in this application, the term "polyolefin" will mean the polyolefin, any combination of polyolefins, including plastomers, elastomers, additives, and the like.

Film Physical Property Modification

It was found that the addition of small amounts of low density polyethylene, the polyolefin/filler blend allowed film extrusion at higher throughput levels with some majority polymers but with little to no reduction in film breathability. Low density polyethylene with a Melt Index of 0.9 to 25 (12 MI being preferred), and a density of 0.900 g/cm³ to 0.930 g/cm³ may be used.

Further improvements in film impact and tear strength are possible by the addition of plastomers, elastomers, styrenic block co-polymers (SIS, SBS, SEBS), EVA, EMA, EEA, or rubbers. Material grades included are listed in Table 2 below.

with good WVTR generally cannot be produced as is taught herein with an amount of filler less than about 16.5 wt.% of the polyolefin/filler composition. Further, it is believed that useful films may not be made with an amount of the filler in excess of about 71.5 wt.%. While at lower than about 16.5 wt.% of filler, the polyolefin/filler composition may not have sufficient breathability. Higher amounts of filler may cause difficulty in compounding and losses in strength of the final breathable film. Generally, the range of filler may be in the range of from about 26 to about 67 wt.%, preferably in the range of from about 33 to about 60 wt.%. The minimum amount of filler is needed to insure the interconnection within the film of voids created at the situs of the filler, particularly by the stretching operation to be subsequently performed. The preferred filler range is from about 30 to about 70 wt.%, based on the total weight of the film. More preferred filler loading is from about 40 to about 60 wt. %.

Fillers useful in certain embodiments of the invention may be any inorganic or organic material or combinations thereof having a low affinity for and a significantly lower elasticity than the polyolefin component or the optional elastomeric component. Preferably, the filler should be a rigid material having a non-smooth surface, or a material which is treated to render its surface hydrophobic. The mean average particle size of the filler is from about 0.5 to about 7 microns, preferably from about 1 to about 5, more preferably from about 2 to about 3.5 microns. It should be understood that smaller particle sizes, such as from about 0.75 to 2, will provide the best balance of compoundability and eventual breathability, but there relative economics makes them generally less useful than particle sizes of 3 microns and above. Such particle sizes are preferred for films having a thickness of from about 0.5–6 mils. Examples of the inorganic fillers include calcium carbonate, talc, clay, kaolin, silica diatomaceous earth, magnesium carbonate, barium carbonate, magnesium sulfate, barium sulfate, calcium sulfate, aluminum hydroxide, zinc oxide, magnesium oxide, calcium oxide, magnesium oxide, titanium oxide, alumina, mica, glass powder, zeolite, silica clay, and com-

TABLE 2

Property Improvement Materials

| Supplier | Grade | Comment 1 | Comment 2 |
|---|---|---|---|
| Exxon Chemical | Exact ™ 3139 | 7.5 MI | Density = 0.900 g/cm³ |
| Exxon Chemical | Exact ™ 4044 | 16.5 MI | Density = 0.895 g/cm³ |
| Exxon Chemical | Exact ™ 9095 | 2.2 MI | Density = 0.893 g/cm³ |
| Exxon Chemical | Exact ™ 3131 | 3.5 MI | Density = 0.900 g/cm³ |
| Exxon Chemical | Paxon ™ SLX 9106 | 2.0 MI | Density = 0.900 g/cm³ |
| Exxon Chemical | Paxon ™ SLX 9101 | 3.5 MI | Density = 0.900 g/cm³ |
| Dexco | Vector ™ 4211 | 13 MI | |
| Dexco | Vector ™ 4411 | 40 MI | |
| Exxon | Vistalon ™ 3708 | EPDM | |
| Exxon | Vistalon ™ 3030 | EPDM | |
| Shell | Kraton ™ G1657 | 8 MI | SEBS |
| Union Carbide | UC 9042 | 5.1 MI | Density = 0.900 g/cm³ |
| Union Carbide | UC 1085 | 0.8 MI | Density = 0.884 g/cm³ |

Filler Materials

To impart breathability to polyolefin films, addition of fillers and subsequent straining is known.

To form the precursor film, fillers may be incorporated at relatively high levels, limited only by the ability of the combination (polyolefin/filler) to be formed into a film. The amount of filler added to the polyethylene depends on the desired properties of the film including tear strength, WVTR, and stretchability. However, it is believed that a film binations thereof, and the like. Calcium carbonate is particularly preferred. The inorganic fillers such as calcium carbonate are preferably surface treated to be hydrophobic so that the filler can repel water to reduce agglomeration of the filler. Also, the surface coating should improve binding of the filler to the polymer while allowing the filler to be pulled away from the polyolefin when the film formed from the polyolefin/filler combination is stretched or oriented. Preferred coatings are stearates, such as calcium stearate, which are generally compliant with FDA regulations. Organic fillers such as wood powder, pulp powder, and other cellulose type powders may be used. Polymer powders such as Teflone® powder and Kevlars® powder may also be included. Combinations of these fillers are also contemplated.

While a broad range of fillers has been described at a broad range of inclusion parameters based on weight percentages, other embodiments are contemplated. For instance, fillers with much higher or much lower specific gravity may be included in the polyolefin at amounts outside the weight ranges disclosed, they will be understood to be contemplated as embodiments of the invention as long as the final film, after orientation has WVTR or drawn down similar to that described herein. For example, while a preferred filler such as calcium carbonate has a density of 2.7 g/cm$^3$, other examples of suitable fillers include, without limitation, hollow glass beads (density=0.3 g/cm$^3$), glass fibers or beads (density=1.11 g/cm$^3$) and barium sulfate (density=4.6 g/cm$^3$).

Compounding of the Polyolefin/Filler Composition

Polyolefin/filler compositions usable in this invention may be compounded in several different ways. The components may be brought into intimate contact by, for example, dry blending these materials and then passing the overall composition through a compounding extruder. Alternatively, the polyolefin and filler components may be fed directly to a mixing device such as a compounding extruder, higher shear continuous mixer, two roll mill or an internal mixer such as a Banbury mixer. Overall, the objective is to obtain a uniform dispersion of the filler in the polymer without agglomeration, and this is readily achieved by inducing sufficient shear and heat to cause the polyolefin component to melt However, time and temperature of mixing should be controlled as is normally done to avoid molecular weight degradation.

Film Extrusion and/or Embossing

Films contemplated by certain embodiments of the present invention may be made utilizing a polyolefin, by processes including, blown, cast, and cast melt embossed, preferred is a cast melt embossed film process. In such extrusion processes, the films of the present invention can be formed into a single layer film, or may be one layer or more of a multi-layer film or film composite. Alternatively, the polyolefin films described in this disclosure can be formed or utilized in the form of a resin blend where the blend components can function to modify WVTR, physical properties, draw-down, sealing, cost, or other functions. Both blend components and functions provided thereby will be known to those of ordinary skill in the art. Films of the present invention may also be included in laminated structures. As long as a film, multi-layer film, or laminated structure includes one or more polyolefin/filler film layers having the WVTR, or draw-down, and the like of the film, it will be understood to be contemplated as an embodiment of the present invention.

The film forming composition (polyolefin/polyolefin blends and filler or fillers) may be manufactured into a precursor film by conventional tubular extrusion (blown bubble process) or by cast extrusion. Film formation by cast extrusion may be more convenient, as the film can be immediately melt embossed as described below.

In the cast extrusion process, the molten resin is extruded from an elongate die in the form of a web. The web may be pulled over at least one patterned embossing roller to chill and solidify the film with an embossed pattern for reasons discussed furher below. The precursor film is may be produced to a gauge of from about 0.5 to 6 mils, preferably from about 0.75 to about 5 mils, more preferably from about 1 to about 4 mils, most preferably from about 1.5 to about 3 mils, which allows for further stretching as described below. However, those of ordinary skill in the art will understand that many factors affect the response of the precursor film to the ring-rolling process. It is our intent that the film or film part of a film composite will have breathability, and at least a minimum of physical properties to maintain its function, that is the film after ring-rolling (either as part of a composite or by itself) should have the ability to perform its function. For instance in the side panel of a diaper, the film might even have substantial voids, providing excellent breathability, but having enough strength to maintain the physical form of the diaper or other article during its use.

The extrusion temperatures, die temperatures, and embossing roller (if used) temperatures will depend on the composition employed, but generally will be in the following ranges for compositions of the present invention prepared by cast extrusion:

| | |
|---|---|
| Melt Temperature (° F.) | 350–550 |
| Die Temperature (° F.) | 350–550 |
| Embossing Roller Temperature (° F.) | 50–130 |

Embossing may be used on the surface of polyolefin films to reduce gloss, although such will not be the films primary function in a ring-rolling process. Embossing can be imposed on the precursor film surface at the time of the film fabrication for cast extrusion, or at a subsequent time for cast or tubular extrusion by procedures well known in the art.

For the present invention, embossing may impose a pattern of different film thicknesses within the precursor film, and can be conducted with an micro/macro pattern, e.g. cross-hatching, dots, lines, circles, diamonds, hexagons, etc. The pattern can be either in line and/or off line and the rollers can be engraved with either pin up and/or pin down type configurations.

Use of the Precursor Film

Traditionally, breathable film has been made using such film precursors as described above, and then orienting the film by a variety of techniques, such as tentering in one or both of the machine direction (MD) or cross or transverse direction (TD). The oriented and breathable film could then be used for a variety of end use articles, such as diapers (usually back sheets, but also top sheets), feminine hygiene items, bandages, catamenial pads, panty liners, incontinent briefs, and the like. However, use of certain embodiments of the present invention will include the precursor film either by itself or a film composite in an interdigitating grooved roller process. By film composite, we intend that one or more additional layers or materials are added or laminated to the film. Such additional materials and layers include synthetic woven, synthetic non-woven, synthetic knit, non-woven, apertured film, macroscopically expanded three-dimensional formed film, filled compositions or laminates and/or a combination of these items. The non-wovens may be made by processes including, but not limited to spunlace, spunbond, meltblown, carded and or air-through or calendar bonded. The materials or layers of the composite can be combined by many method known to those of ordinary skill. For instance, adhesives (including spray adhesives, hot melt adhesives, latex based adhesives and the like), thermal bonding, ultra-sonic bonding, extrusion lamination, needle punching, and the like. For instance, in the manufacture of infant diapers, toddler training pants, adult incontinence devices, feminine hygiene items, medical gowns, medical drapes, and house wrap, parts or all of the final product may be assembled (by for instance heat or adhesive lamination) then the partial or finished construction is passed through one or more pairs of interdigitating grooved rollers to render the precursor film high in WVTR.

Stretching

High WVTR film, film composites or fabricated articles made therefrom may achieved by stretching the precursor film to form interconnected voids prior to ring-rolling. Stretching or "orientation "of the film may be carried out monoaxially in the machine direction (MD) or the transverse direction (TD) or in both directions (biaxially) either simultaneously or sequentially using conventional equipment and processes following cooling of the precursor film.

Blown films are preferably stretched in the machine direction or in both directions whereas cast films are preferably stretched in the transverse direction. For orientation in the MD, the precursor film is passed around two rollers driven at different surface speeds and finally to a take up roller. The second driven roller which is closest to the take up roller is driven faster than the first driven roller. As a consequence the film is stretched between the driven rollers.

Stretching of melt embossed precursor films either using both a tentering device and a directly in a ring-rolling device or just the ring-rolling device produces breathable films having the desired water vapor permeability. The resulting films had greater permeability in the areas of reduced thickness in comparison to the areas of greater thickness.

Preferably, the film is stretched through a pair or pairs of interdigitating rollers. In this embodiment machine direction orientation is accomplished by stretching the film through a gear like pair of rollers. Transverse direction orientation is accomplished by stretching the film through a pair of disk like rollers. The preferred embodiment employs rollers with a tooth pitch, W=0.080", however a pitch of 0.040" to 0.500" is acceptable. The tooth depth (d), is preferably 0.1 00", however a depth of 0.030" to 0.500" is acceptable (see FIG. 4). For the transverse direction orientation rollers, the depth may be up to 1" as mechanical interference is less of an issue with the TD rollers. The preferred embodiment employs interdigitating grooved rollers that can be temperature controlled from 50° F. to 210° F., more preferred is a range of from 70° F.–190° F., more preferred is 85° F.–180° F., most preferred is 95° F.–159° F. Roller temperature may be maintained through internal liquid, electrical systems, an external source of cooling/heating, combinations thereof, and other methods which will be apparent to those of ordinary skill in the art. The preferred embodiment is internal liquid cooled/heated rollers.

The depth of engagement of the roller teeth determines the amount of orientation imparted on the film. A balance must be drawn between the depth of engagement and the level of filler in the film as many properties are affected as depicted in Table 3 below.

TABLE 3

Relationships Between Process Factors and Resulting Film Properties

| Increasing Process Factor | WVTR | Dart Impact | Basis Weight | CD Tensile | MD Tear |
|---|---|---|---|---|---|
| $CaCO_3$ | Increase | Decrease | | | Decrease |
| MD Orientation | Increase | Decrease | Decrease | | Decrease |
| TD Orientation | Increase | Decrease | Decrease | Decrease | |
| Roll Temperature | Increase | | Decrease | | |

Although not thoroughly investigated, controlling of the strain on the film during stretching is believed to be important to controlling the WVTR. For stretching in the transverse direction, strain is controlled for a given stretch ratio by adjusting the film speed and the stretching distance. The stretching distance is measured, between the point where the film starts to increase in width to the closest point where the film is fuilly stretched. For stretching in the machine direction, strain is controlled for a given stretch ratio by controlling film speed and the gap between the first and second driven rollers.

A range of stretching ratios from 1:2 to 1:5 prove satisfactory for MD stretching with a ratio of 1:4 being preferred. A range of stretching ratios of 1:2 to 1:5 prove satisfactory for TD stretching with a ratio of 1:4 being preferred.

It is a further object of this invention to provide such a process for producing a barrier layer having high liquid strikethrough resistance.

The process of ring-rolling also may activate the elasticity of the web (dependent upon specific ring-rolling pattern used), in addition to imparting breathability to the web.

Precursor webs containing elastomeric components add to the elasticity developed during the ring-rolling process.

Ring-Rolling Process

To illustrate the process, the term web or webs are used. As used herein, the term web will include a precursor film and optionally one or more additional webs or layers, as discussed above, for instance one or more non-woven webs and/or one or more film webs. Such web components can be pre-assembled or laminated. Prior to ring-rolling, at least one additional web may be added. Web 10 and alternatively optional web 11 may be webs of a precursor film with either another film or fabric (11) the precursor film will have a thickness from 0.5 to 6 mils. For example, the optional web 11 may be melt-blown webs of the type taught in the article entitled "Superfine Thermoplastic Fibers" by Van A. Wente, appearing in *Industrial Engineering Chemistry*, Aug., 1956, Vol. 48, No. 8 (pages 1342–1346). While melt-blown material may be nylon, polyester, or any polymer or polymer blend capable of being melt-blown, a melt-blown polypropylene web is preferred. A melt-blown web could comprise two or more zones of different melt-blown polymers. Melt-blown webs having a basis weight of up to about 30 g/m² or greater can be used in the present invention, but lower weight webs are generally preferred in order to minimize the cost of the barrier layer produced therefrom. Technology provides for the production of melt-blown webs with a minimum basis weight of about 3 g/m², but available commercial melt-blown webs generally have a basis weight of 10 g/m² or more. The preferred basis weight for optional web 11 is from about 10 g/m² to about 30 g/m²; most preferably from about 10 g/m² to about 20 g/m². The density of melt-blown optional web 11 is preferably up to about 0.15 g/cm$^3$ and most preferably up to about 0.1 g/cm$^3$. Web 10 and optional web 11 may be the same or different.

Web 10 and (when present) optional web 11 have preferably been rolled up together as plies with adjacent surfaces on feed roller 20. They are unrolled from feed roller 20 retaining their contiguous relationship and passed into the nip of interdigitating grooved rollers 24 and 25. Grooved rollers 24 and 25 have grooves perpendicular to the axis of the rollers (parallel to the machine direction) as shown in FIG. 2 which is a sectional view of grooved rollers 24 and 25 taken along line 2—2 of FIG. 1.

It has been found that the web and optional web 11 will be stretched more uniformly with less tendency to tear the webs when interdigitating grooved rollers 24 and 25 are heated. The rollers are preferably heated such that their surface temperature are within the range of about 160° F. to 220° F.; more preferably within the range of 180° F. to 200° F.

Figure 2:
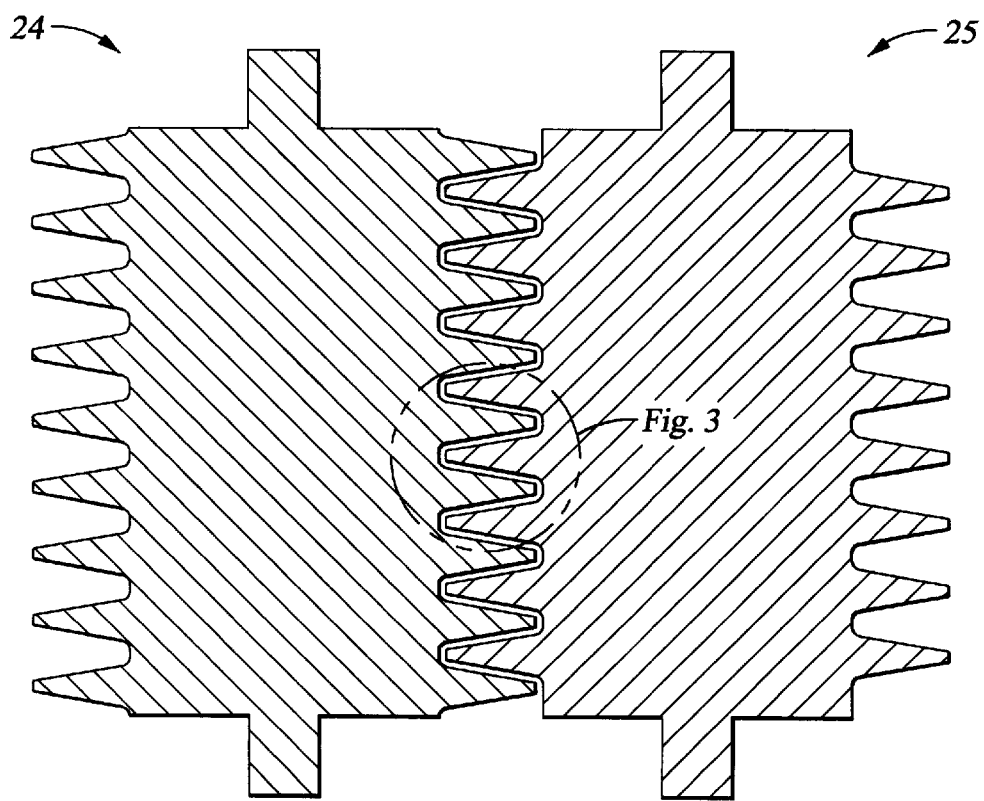
FIG. 2 illustrates a cross-sectional view of the interdigitating grooved rollers of FIG. 1, taken along the lines 2—2.
Figure 4:
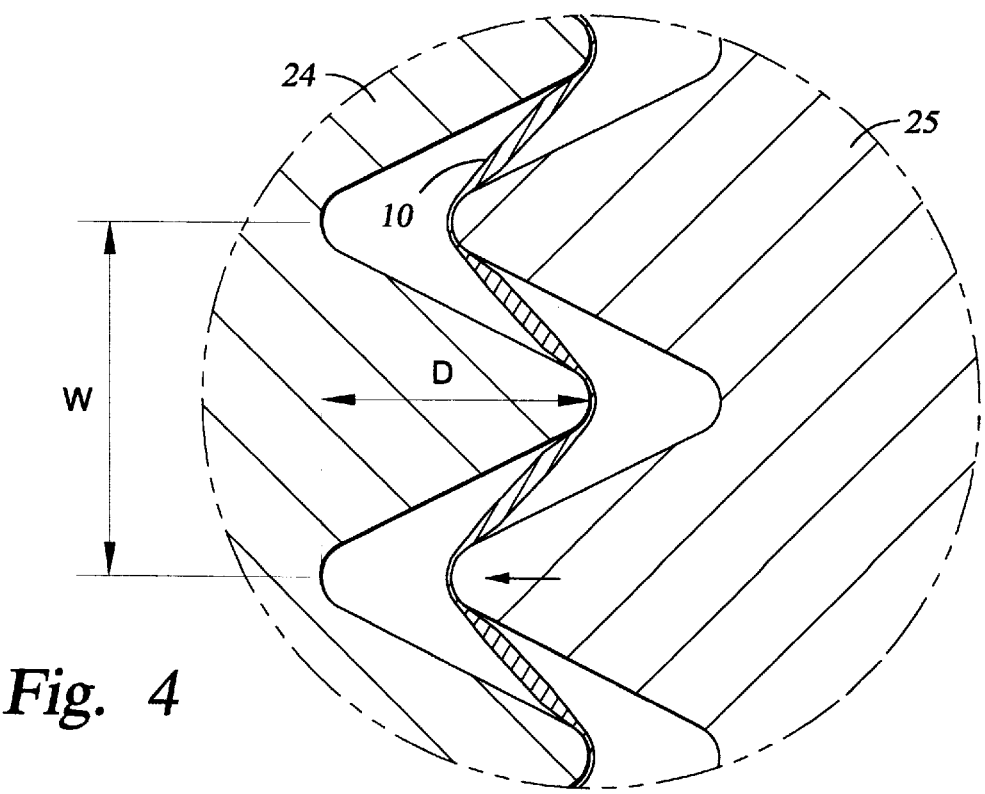
FIG. 4 shows how a film is stretched with interdigitating rollers.

FIG. 1 shows a preferred arrangement of interdigitating grooved rollers 24 and 25 being located with their centers in a horizontal plane and webs 10 and 11 contacting the surface of roll 24 for about one-fourth of a revolution before entering the nip between rollers 24 and 25; this provides an opportunity for the web or webs 10 and optional web 11 to be heated prior to entering the nip. However, interdigitating grooved rollers 24 and 25 could be positioned with their centers in a vertical plan or at any other angle and web 10 and optional web 11 could be fed directly into the nip of the rollers. Preheating of webs 10 and 11 if found to be necessary in order to avoid tearing of the webs, could be accomplished in any conventional manner FIG. 4 illustrates how the web 10 is stretched between the interdigitating grooved rollers 24 and 25.

The webs where two or more webs are fed is stretched and enmeshed while passing between the interdigitating grooved rollers 24 and 25 and are thus lightly bonded together producing final product 12. Where final improved WVTR composite film 12 has been stretched in the cross-machine direction by the grooved rollers 24 and 25 of FIGS. 1 and 2, a device such as a curved Mount Hope roll 26 or tenter clamps is needed to extend the now high WVTR film or film composite to its fullest width. The extended and smoothed film 12 is then rolled up on a takeup roller 27.

The amount of lateral stretch imparted to web plies by the grooved rollers 24 and 25 will depend on the shape and depth of the grooves of the rollers, and on the gap spacing between the rollers.

U.S. Pat. No. 4,223,059, issued to Eckhard Calif. Schwarz on Sep. 16, 1980 discloses interdigitating rollers having grooves of generally sine-wave shape cross-section which may be used for the present invention. U.S. Pat. No. 4,153,664 issued to Rinehardt N. Sabee on May 8, 1979, discloses the stretching of polymeric webs by ring-rolling with rollers having grooves with a variety of shapes. The shape of the grooves of the rollers will generally determine whether the web is stretched uniformly or at incremental, spaced portions of the web. Incremental stretching of the web is more likely to cause some local tearing of film or film composites which would damage the liquid strikethrough resistance of the film and, therefore, is not preferred for the present invention.

Figure 3:
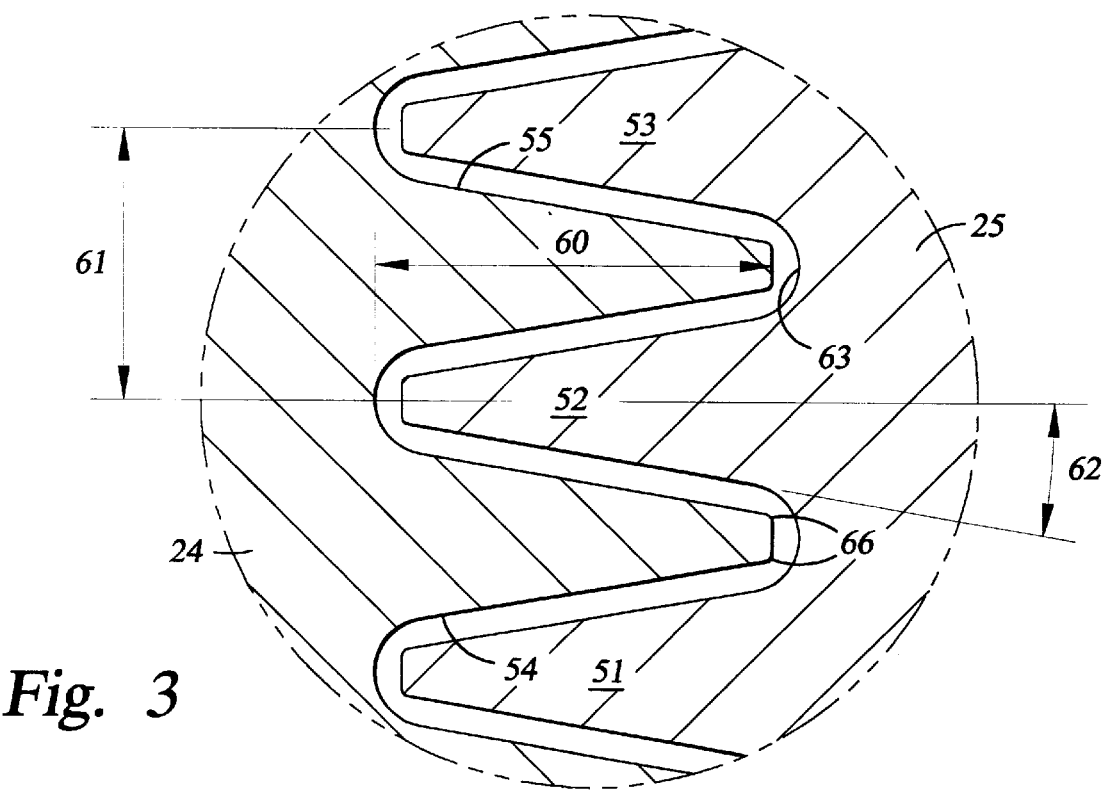
FIG. 3 illustrates an enlarged view of area 3 from FIG. 2 showing several interdigitating teeth from the grooved rollers.

A preferred groove pattern for interdigitating rollers 24 and 25 is shown in FIG. 3 which is an enlarged view of area 3 of FIG. 2. FIG. 3 shows a partial cutaway view of interdigitating rollers 24 and 25. Teeth 54 and 55 of grooved roller 24 intermesh with teeth 51, 52 and 53 of grooved roller 25. The length 60 of the teeth is 3.81 mm, and the distance 61 between the centerlines of adjacent teeth on each roller is 2.54 mm. The teeth have generally straight sides which are at an angle 62 from a plane perpendicular to the axis of rollers 24 and 25 of 9'17". The land at the base of the teeth has a radius 63 of 0.51 mm. Sharp corners 66 at the ends of the teeth are removed.

It is preferred that the interdigitating grooves of rollers 24 and 25 be perpendicular to the axis of the rollers. In this way, the maximum number of grooves of a given size will engage the web 10 and 11 at the same time and impact stretch to the webs. By having the maximum number of teeth engage the web at a given time, a more uniform stretching of the webs is achieved so that local tearing of the film or film composite is minimized. The stretched film 12 can be easily smoothed in the cross-machine direction.

A reproducible gap setting between grooved rollers 24 and 25 can be achieved by having the bearing of one of the grooved rollers, e.g. 24, stationary while those of the other grooved roller 25 can be moved in the horizontal direction. Grooved roller 25 is moved in the horizontal direction. Grooved roller 25 is moved toward roll 24 until its teeth are intenneshed with those of grooved roller 25 and it will move no firther. The bearings of grooved roller 25 are then moved away from grooved roller 24 a measured distance, the gap setting. The preferred gap setting for practicing the present invention are from about 0.76 mm. to about 1.65 mm. With grooved rollers 24 and 25 having a tooth configuration as shown in FIG. 3 and described above, the maximum width of film or film composite layer 12 which can be achieved for a single pass is about 2½ to 3 times the width of starting webs 10 and 11. By incising the gap between grooved rollers 24 and 25, the amount of lateral stretch imparted to webs 10 and 11 is decreased. Therefore, the width of film or film composite 12 compared to the width of starting web can be varied for a single pass between grooved rollers 24 and 25 from a maximum increase of 2½ to 3 times to no increase by the appropriate gap setting.

If it is desired to stretch the web more than can be achieved by a single pass between the grooved rollers, multiple passes between grooved rollers 24 and 25 can be used.

Basis weight is generally an important property desired to be controlled for film or film composite layer (total ring-rolled web) 12. For cost reasons, the lightest film or film composite that will provide sufficient breathability is desired. A basis weight of the film produced by itself will be generally above 20 g/cm$^2$. The desired basis weight can be obtained by controlling the amount of stretch imparted to web 10 and optional web 11 by grooved rollers 24 and 25 as described above, and by the selection of the basis weights of the starting webs 10 and 11. For the present invention, starting webs 10 and 11 have a cumulative basis weight in the range of about 1.1 to 4 times the ultimate desired basis weight, preferably in the range of about 1.5 to 3 times the desired basis weight, most preferably about 2 times the desired basis weight. Correspondingly, the desired width of breathable film or film composite 12 can be achieved by selecting a proper combination of stretch imparted by the grooved rollers 24 and 25 and initial width of starting webs 10 and 11. For the present invention, the initial width of starting webs 10 and 11 before passing between grooved rollers 24 and 25 is within the range of about 0.9 to about 0.25 times the desired width, preferably within the range of about 0.7 to about 0.3 times the desired width, most preferably about 0.5 times the desired width.

Properties of films produced

WVTR

In an embodiment of the present invention, certain films and articles made therefrom have higher WVTR than previously thought possible. The WVTR of such films are greater than 100 g/m$^2$/24 hr @ 37.8° C., 100% RH, preferably greater than 1000, and more preferably greater than 2000 g/m$^2$/24 hr @ 37.8° C., 100% RH. Some applications benefit from film with a WVTR at or greater than 10,000 g/m$^2$/24 hr @ 37.8° C., 100% RH.

Test Procedures

The test procedures used to determine the unique properties of the layers of the present invention and to provide the test results in the examples below are as follows:

Water Vapor Transmission Rate (WVTR)

Both a Mocon W1, and a Mocon W600 instrument are used to measure water evaporated from a sealed wet cell at 37.8° C. through the test film and into a stream of dry air or nitrogen. It is assumed that the relative humidity on the wet side of the film is approximately 100%, and the dry side is approximately 0%. The amount of water vapor in the air stream is precisely measured by a pulse modulated infra red (PMIR) cell. Following appropriate purging of residual air, and after reaching a steady state water vapor transmission rate, a reading is taken. WVTR of the test films are reported as grams of water/meter$^2$/day. The output of the unit is calibrated to the results obtained with a film of known WVTR The testing protocols are based on ASTM F1249-90.

Mocon W1

The Mocon W1 has a single test cell and an analog chart recorder. Air is pumped through a desiccant dryer, then through the test cell, and then past the PMIR sensor. A 5 minute purge of residual air is followed by a 6 minute test cycle with controlled air flow. The result is a steady state value for WVTR. The purge and test cycles are controlled manually. The unit is calibrated to a film with a known WVTR every 12 hours. Calibration results are control charted and adjustments are made to the instrument calibration accordingly.

Mocon W600

The Mocon W600 has 6 measurement cells with PMIR data fed into a computer. Nitrogen is fed through a desiccant dryer, then through the active test cell, then past the PMIR sensor. In addition to data compilation, the computer controls test cycle sequencing. All cells are purged simultaneously for an 8 minute period. This is followed by an 8 minute test cycle for each of the six cells. Total testing time is 56 minutes. Two of the test cells always measure reference films with a known WVTR.

Gurley Porosity

Teleyn Gurley Model 4190 Porosity Tester with sensitivity attachment is used. The procedure is as follows:

a) Cut a strip of film (~2" wide) across the entire web width, b) Insert a film sample to be tested between orifice plates, c) Set the sensitivity adjustment on "5", d) Turn the inner cylinder so that the timer eye is vertically centered below the 10 cm$^3$ silver step on the cylinder, e) Reset the timer to zero, f) Pull the spring clear of the top flange and releasing the cylinder, When the timer stops counting, the test is completed. The number of counts is multiplied by 10 and the resulting number is "Gurley seconds per 100 cm$^3$".

It will be appreciated by those of ordinary skill in the art that the films of m-polyethylene resins of certain embodiments of the present invention, can be combined with other materials, depending on the intended function of the resulting film.

Other methods of improving and/or controlling WVTR properties of the film or container may be used in addition to the methods described herein without departing from the intended scope of the invention. For example, mechanical treatment such as micro pores.

Liquid Column Strikethrough Resistance Test

The liquid strikethrough resistance test is a method for determining the water pressure in millimeters of water at which water penetrates a repellent barrier layer at a specified fill rate and with the water and barrier layer at a specified temperature. Such a test is described in *INDA Journal*, Vol. 5, No. 2, Karen K. Leonas; the strikethrough resistance of embodiments of the invention are from 50–500 cm.

The following non-limiting examples are provided for illustrative purposes only.

EXAMPLES

Examples 1–12

LLDPE/CaCO$_3$ films are made utilizing the following conditions, materials and equipment shown in Table 4.

Examples 1–12 used LL-3003.09 (a 3 Ml, 0.917 g/cm$^3$ polyethylene (Z-N) available from Exxon Chemical Co., Houston, Tex.) containing levels of CaCO$_3$ as shown in Table 4, blended with 100 parts of LL-3003.

Examples 13–16

Example 13–16 were made under the conditions shown in Table 4, Examples 1–12, but with Exceed® ECD-112 (a 3.4 Ml, 0.917 g/cm$^3$ density m-LLDPE from Exxon Chemical Co., Houston, Tex.) with filler, master batch (MB) and elastomer levels as shown in Table 5.

Examples 1–4, 9, 10, 11, 12, 13, 14 and 15 were run on a Davis Standard cast line. Examples 9, 10, 11, 12, 14, and 15 were oriented in the TD, Example 9 10, 11, 12, and 15 were further MD drawn. Examples 5, 6, 7, 8, and 16 were run on a blown film extruder.

Each film sample was run through various ring-rolling apparatus as shown in Tables 5, 6 and 7, with the results for basis weight shown in Table 5, the results for WVTR in Table 6, the results for air porosity shown in Table 7.

TABLE 4

| Condition | Example 1 | Example 2 | Example 3 | Example 4 | Example 5 | Example 6 | Example 7 | Example 8 |
|---|---|---|---|---|---|---|---|---|
| Material | A | B | B | B | C | D | E | F |
| Process | Cast/TD | Cast | Cast | Cast | Blown | Blown | Blown | Blown |
| Ext. RPM | 17 | 6 | 8 | 11 | 45 | 65 | 65 | 61 |
| Screen PSI | 2600 | 2150 | 2380 | 2800 | 5290 | 6000 | 5730 | 6300 |
| Die PSI | 940 | 750 | 810 | 900 | N/A/ | N/A | N/A | N/A |
| Melt Temp | 390 | 374 | 378 | 388 | 400 | 410 | 411 | 430 |
| Up Width | 23 | 28 | 28 | 28 | 9 | 11 | 11 | 11 |
| Down Width | 62.4 | N/A | N/A | N/A | N/A | N/A | N/A | N/A |
| FPM | 165 | 65 | 77 | 102 | 30 | 28 | 30 | 28 |
| MD Drawn | N/A | N/A | N/A | N/A | N/A | N/A | N/A | N/A |

| Condition | Example 9 | Example 10 | Example 11 | Example 12 | Example 13 | Example 14 | Example 15 | Example 16 |
|---|---|---|---|---|---|---|---|---|
| Material | G | B | H | B | B | B | B | E |
| Process | Cast/TD/MD/Drawn | Cast/TD/MD Drawn | Cast/TD/MD Drawn | Cast/TD/MD Drawn | Cast | Cast/TD | Cast/TD/MD Drawn | Blown |
| Ext. RPM | 15 | 21 | 15 | 22 | 19 | 19 | 19 | 35 |
| Screen SPI | 3600 | 3440 | 3138 | 3302 | 3740 | 3740 | 3740 | 4750 |
| Die PSI | N/A | N/A | N/A | N/A | 1270 | 1270 | 1270 | N/A |
| Melt Temp | 414 | 402 | 390 | 350 | 430 | 430 | 430 | 425 |
| Up Width | 21 | 21 | 21 | 24 | 22 | 22 | 22 | 10 |
| Down Width | 83 | 77 | 82 | 89 | N/A | 63 | 63 | N/A |
| FPM | 181 | 195 | 186 | 140 | 340 | 340 | 340 | 25 |
| MD Drawn | 1:3 | 1:3 | 1:3 | 1:3 | N/A | N/A | 1:3 | N/A |

| Material | LLDPE | CaCO₃ | EVA | SBS |
|---|---|---|---|---|
| A | 63% | 37% | | |
| B | 50% | 50% | | |
| C | 40% | 40% | 8% | 12% |
| D | 35% | 35% | 12% | 18% |
| E | 30% | 30% | 16% | 24% |
| F | 40% | 40% | 20% | |
| G | 55% | 45% | | |
| H | 53% | 47% | | |

TABLE 5

BASIS WEIGHT (Grams/Square Meter)

| | PROPERTIES BEFORE ACTIVATION | | | | | PROPERTIES AFTER ACTIVATION | | | | |
|---|---|---|---|---|---|---|---|---|---|---|
| Example | Mat. Comp.** | Mfg. Meth.* | Weight g/m² | WVTR | Air Porosity sec/100 cm³ | Type 1 Manual Stretch | Type 2 Ring-Roll 0.400 DOE | Type 3 Ring-Roll 0.175 DOE | Type 4 Ring-Roll 0.100 DOE | Type 5 Tooth Pattern |
| 1 | A | AA | 22 | 1318 | >10000 | | Destroyed | Destroyed | 21 | N/A |
| 2 | B | BB | 79 | <100 | N/A | | 23 | N/A | N/A | N/A |
| 3 | B | BB | 86 | <100 | N/A | | 25 | N/A | N/A | N/A |
| 4 | B | BB | 108 | <100 | N/A | | 29 | N/A | N/A | N/A |
| 5 | C | CC | 53 | <100 | N/A | | | N/A | N/A | |
| 6 | D | CC | | <100 | N/A | | | N/A | N/A | |
| 7 | E | CC | 49 | <100 | N/A | | 21 | N/A | N/A | |
| 8 | F | CC | 54 | <100 | N/A | | | N/A | N/A | |
| 9 | G | DD | 18 | 8000 | 190 | | Destroyed | | N/A | N/A |
| 10 | B | DD | 25 | 7000 | 300 | | Destroyed | | N/A | N/A |
| 11 | H | DD | 20 | 6100 | 642 | | Destroyed | | N/A | N/A |
| 12 | B | DD | 36 | 7100 | 898 | | Destroyed | | N/A | N/A |
| 13 | B | BB | 73 | <100 | N/A | 29 | | | | |
| 14 | B | AA | 23 | 7900 | 210 | | | | | |
| 15 | B | DD | 21 | 8000 | 263 | 22 | | | | |
| 16 | B | CC | 22 | <T00 | N/A | 11 | | | | |

*Compositions of Raw Materials

| | LLDPE | CaCO₃ | EVA | SBS |
|---|---|---|---|---|
| A | 63% | 37% | | |
| B | 50% | 50% | | |
| C | 40% | 40% | 8% | 12% |
| D | 35% | 35% | 12% | 18% |
| E | 30% | 30% | 16% | 24% |
| F | 40% | 40% | 20% | |

TABLE 5-continued

BASIS WEIGHT (Grams/Square Meter)

G 55% 45%
H 53% 47%

**Manufacturing Methods

AA CAST/TD
BB CAST
CC BLOWN
DD CAST/TD/MD DRAWN

TABLE 6

WATER VAPOR TRANSMISSION RATE (g/square meter/24 hours)

| | PROPERTIES BEFORE ACTIVATION | | | | | PROPERTIES AFTER ACTIVATION | | | | |
|---|---|---|---|---|---|---|---|---|---|---|
| | | | | | | Type 1 | Type 2 | Type 3 | Type 4 | Type 5 |
| Example | Mat. Comp.** | Mfg. Meth.* | Weight g/m² | WVTR | Air Porosity sec/100 cm³ | Manual Stretch | Ring-Roll 0.400 DOE | Ring-Roll 0.175 DOE | Ring-Roll 0.100 DOE | Tooth Pattern |
| 1 | A | AA | 22 | 1318 | >10000 | | Destroyed | Destroyed | 750 | N/A |
| 2 | B | BB | 79 | <100 | N/A | | 1300 | N/A | N/A | N/A |
| 3 | B | BB | 86 | <100 | N/A | | 1300 | N/A | N/A | N/A |
| 4 | B | BB | 108 | <100 | N/A | 1600 | 1100 | N/A | N/A | N/A |
| 5 | C | CC | 53 | <100 | N/A | 400 | 360 | N/A | N/A | 800 |
| 6 | D | CC | | <100 | N/A | 200 | 350 | N/A | N/A | 400 |
| 7 | E | CC | 49 | <100 | N/A | 200 | 290 | N/A | N/A | 200 |
| 8 | F | CC | 54 | <100 | N/A | 200 | 240 | N/A | N/A | 450 |
| 9 | G | DD | 18 | 8000 | 190 | | Destroyed | 7100 | N/A | N/A |
| 10 | B | DD | 25 | 7000 | 300 | | Destroyed | 9200 | N/A | N/A |
| 11 | H | DD | 20 | 6100 | 642 | | Destroyed | 9000 | N/A | N/A |
| 12 | B | DD | 36 | 7100 | 898 | 6900 | Destroyed | 7850 | N/A | N/A |
| 13 | B | BB | 73 | <100 | N/A | 1400 | | | | |
| 14 | B | AA | 23 | 7900 | 210 | 6400 | | | | |
| 15 | B | DD | 21 | 8000 | 263 | 7350 | | | | |
| 16 | B | CC | 22 | <100 | N/A | 2600 | | | | |

*Compositions of Raw Materials

| | LLDPE | CaCO₃ | EVA | SBS |
|---|---|---|---|---|
| A | 63% | 37% | | |
| B | 50% | 50% | | |
| C | 40% | 40% | 8% | 12% |
| D | 35% | 35% | 12% | 18% |
| E | 30% | 30% | 16% | 24% |
| F | 40% | 40% | 20% | |
| G | 55% | 45% | | |
| H | 53% | 47% | | |

**Manufacturing Methods

AA CAST/TD
BB CAST
CC BLOWN
DD CAST/TD/MD DRAWN

TABLE 7

AIR POROSITY (Seconds/100 cm³/Square inch)

| | PROPERTIES BEFORE ACTIVATION | | | | | PROPERTIES AFTER ACTIVATION | | | | |
|---|---|---|---|---|---|---|---|---|---|---|
| | | | | | | Type 1 | Type 2 | Type 3 | Type 4 | Type 5 |
| Example | Mat. Comp.** | Mfg. Meth.* | Weight g/m² | WVTR | Air Porosity sec/100 cm³ | Manual Stretch | Ring-Roll 0.400 DOE | Ring-Roll 0.175 DOE | Ring-Roll 0.100 DOE | Tooth Pattern |
| 1 | A | AA | 22 | 1318 | >10000 | | Destroyed | Destroyed | >10000 | N/A |
| 2 | B | BB | 79 | <100 | N/A | | 4165 | N/A | N/A | N/A |
| 3 | B | BB | 86 | <100 | N/A | | 9966 | N/A | N/A | N/A |
| 4 | B | BB | 108 | <100 | N/A | | 5685 | N/A | N/A | N/A |
| 5 | C | CC | 53 | <100 | N/A | | >10000 | N/A | N/A | 890 |
| 6 | D | CC | | <100 | N/A | | >10000 | N/A | N/A | 6320 |
| 7 | E | CC | 49 | <100 | N/A | | >10000 | N/A | N/A | >10000 |

TABLE 7-continued

AIR POROSITY (Seconds/100 cm³/Square inch)

| 8 | F | CC | 54 | <100 | N/A | | >10000 | N/A | N/A | 640 |
|---|---|----|----|------|-----|---|--------|-----|-----|-----|
| 9 | 0 | DD | 18 | 8000 | 190 | | Destroyed | 33 | N/A | N/A |
| 10 | B | DD | 25 | 7000 | 300 | | Destroyed | 48 | N/A | N/A |
| 11 | H | DD | 20 | 6100 | 642 | | Destroyed | 5 | N/A | N/A |
| 12 | B | DD | 36 | 7100 | 898 | | Destroyed | 17 | N/A | N/A |
| 13 | B | BB | 73 | <100 | N/A | | | | | |
| 14 | B | AA | 23 | 7900 | 210 | | | | | |
| 15 | B | DD | 21 | 8000 | 263 | 258 | | | | |
| 16 | B | CC | 22 | <100 | N/A | | | | | |

*Compositions of Raw Materials

|   | LLDPE | CaCO₃ | EVA | SBS |
|---|-------|-------|-----|-----|
| A | 63% | 37% | | |
| B | 50% | 50% | | |
| C | 40% | 40% | 8% | 12% |
| D | 35% | 35% | 12% | 18% |
| E | 30% | 30% | 16% | 24% |
| F | 40% | 40% | 20% | |
| G | 55% | 45% | | |
| H | 53% | 47% | | |

**Manufacturing Methods

AA    CAST/TD
BB    CAST
CC    BLOWN
DD    CAST/TD/MD DRAWN

Example 17

A blend of 57% ECC FilmLink 400 CaCO₃ was combined with 33% Exxon PD 7623 Impact Copolymer, 2% Exxon LD-200.48, and 8% Exxon Exact 3131 oriented in interdigitating rollers of 0.080" pitch. The MD depth of engagement was 0.020", and the TD depth of engagement was 0.040". The temperature of the interdigitating grooved rollers was 140° F.

Example 18

A blend of 57% ECC FilmLink 400 CaCO₃ was combined with 33% Exxon PD 7623 Impact Copolymer, 2% Exxon LD-200.48, and 8% Exxon Exact 3131 oriented in interdigitating rollers of 0.080" pitch. The MD depth of engagement was 0.020", and the TD depth of engagement was 0.040". The temperature of the interdigitating grooved rollers was 110°F.

Example 19

A blend of 57% ECC FilmLink 400 CaCO₃ was combined with 33% Exxon PD 7623 Impact Copolymer, 2% Exxon LD-200.48, and 8% Exxon Exact 3131 oriented in interdigitating rollers of 0.080" pitch. The MD depth of engagement was 0.020", and the TD depth of engagement was 0.040". The temperature of the interdigitating grooved rollers was 70° F.

As can be seen from Table 8, the WVTR rise from a roller temperature of 70° F. (considered ambient temperature) to 110° F. then 140° F. is dramatic, unexpected and surprising. It would be expected that heating the film would soften it and the polymer would not tear away from the filler as easily. Such a result would likely cause fewer or smaller pores, and thereby reduced WVTR. Accordingly, the significant increase in WVTR produced by using heated rollers is both surprising and unexpected.

TABLE 8

|   | Example 17 | Example 18 | Example 19 |
|---|------------|------------|------------|
| Roller Temperature (° F.) | 140 | 110 | 70 |
| Basis Weight (g/m²) | 43 | 40 | 39 |
| WVTR (g/m²/day) | 4100 | 3000 | 1900 |
| Dart Impact (g) | 240 | 300 | 300 |
| MD Ultimate (g/in) | 1585 | 1532 | 1453 |
| MD Elongation (%) | 408 | 431 | 442 |
| TD @ 5% (g/in) | 457 | 389 | 388 |
| TD Ultimate (g/in) | 785 | 1166 | 1049 |
| TD Elongation (%) | 351 | 358 | 357 |
| MD Elmendorf Tear (g) | 166 | 208 | 205 |

A linear regression analysis reveals that with the above fixed formulation, depth of activation water vapor transmission rate is predicted by the following equation:

$$WVTR = -329.73 + 31.216 \text{ Roller Temperature (°F.)}$$

Example 20

A blend of 52% ECC FilmLink 400 CaCO₃ was combined with 48% Exxon PD 7623 Impact Copolymer Polypropylene. Film was oriented off line with interdigitating rolls of 0.100" pitch. The MD depth of engagement was 0.030' and the TD depth of engagement was 0.019".

Example 21

A blend of 52% ECC FilmLink 400 CaCO₃ was combined with 40% Exxon PD 7623 Impact Copolymer, 2% Exxon LD-202.48, and 6% Exxon SLX9101. Film was oriented in interdigitating rolls of 0.080" pitch. The MD depth of engagement was 0.028", and the TD depth of engagement was 0.034".

Example 22

A blend of 55% ECC FilmLink 400 CaCO₃ was combined with 31% Exxon PD 7623 Impact Copolymer, 4% Exxon LD-202.48, 2% Ampacet 110131 TiO$_2$ concentrate, and 8% Exxon Exact 3131. Film was oriented in interdigitating rolls of 0.080" pitch. The MD depth of engagement was 0.021", and the TD depth of engagement was 0.037".

Table 9 demonstrates the high absolute values of tear and impact strength relative to known polypropylene breathable films. Also shown is the further property improvement made by the addition of minority amounts of other polyolefins.

TABLE 9

Film Properties

|  | Example 20 | Example 21 | Example 22 |
|---|---|---|---|
| Basis Weight (g/m$^2$) | 41.0 | 40.6 | 40.3 |
| WVTR (g/m$^2$/day) | 1457 | 1462 | 1400 |
| Dart Impact (g) | 210 | 315 | 315 |
| MD Ultimate (g/cm) | 625 | 609 | 604 |
| MD Elongation (%) | 423 | 482 | 448 |
| TD @ 5% (g/cm) | 231 | 151 | 140 |
| TD Ultimate (g/cm) | 367 | 501 | 440 |
| TD Elongation (%) | 410 | 464 | 398 |
| Light Transmission (%) | 45 | 43 | 39 |
| MD Elmendorf Tear (g) | 79 | 195 | 198 |

While the present invention has been described and illustrated by reference to particular embodiments thereof, it will be appreciated by those of ordinary skill in the art that the invention lends itself to variations not necessarily illustrated herein. For example, it is not beyond the scope of this invention to include additives with the claimed improved, high WVTR film process. For this reason, then, reference should be made to the appended claims and the remainder of the specification for purposes of determining the true scope of the present invention.

What is claimed is:

1. A process for producing a breathable film having a WVTR greater than 200 g/m$^2$/day at 38° C. and 90% relative humidity comprising a polyolefin and a filler, said process comprising:
    a) extruding a precursor film from a polyolefin blend comprising at least a first polymer composition and a second polymer composition and said filler, said filler having a concentration in a range of from about 16.5 to about 71.5 wt.% of said polyolefin blend; and
    b) passing said precursor film between at least one pair of interdigitating grooved rollers to stretch said precursor film, said rollers being heated to a temperature range of from 95° F. to 159° F., so that said precursor film contacting said rollers is heated and stretched to produce a breathable film having permanent elongation, said breathable film having a WVTR greater than 200 g/m$^2$/day at 38° C. and 90% relative humidity, wherein said WVTR of said breathable film produced is higher when said rollers are heated to the highest temperature within said temperature range than said WVTR of said breathable film produced at the lowest temperature within said temperature range.

2. The process of claim 1 wherein said polyolefin is selected from the group consisting of polypropylene, polyethylene, ethylene polar comonomer polymers, ethylene α-olefin copolymers and combinations thereof.

3. The process of claim 1 further comprising cooling said precursor film to a temperature of at least 75° F. or less after step a) but prior to step b).

4. The process of claim 1 wherein said rollers are heated to a temperature range of from about 110° F. to about 140° F.

5. The process of claim 1 wherein at least one of the polymer compositions comprises an elastomer.

6. A process for producing a breathable film having a WVTR of at least 200 g/m$^2$/day at 38° C. and 90% relative humidity comprising a polyolefin blend, said polyolefin blend having at least a first and a second polymer composition, and a filler, said process comprising:
    a) extruding a precursor film from said polyolefin blend comprising said first and said second polymer compositions and said filler, said filler concentration being in a range of from about 16.5 to about 71.5 wt.% of said polyolefin blend, wherein,
       i) said first polymer composition is a polypropylene and
       ii) said second polymer composition is selected from the group consisting of elastomers, plastomers, styrenic block copolymers, ethylene-maleic anhydride copolymers, ethylene ethyl acetate, and combinations thereof; and
    b) passing said precursor film between at least one pair of interdigitating grooved rollers to stretch said precursor film, said rollers being heated to a temperature range of from 95° F. to 159° F. so that said precursor film contacting said rollers is heated and stretched to produce said breathable film having permanent elongation, so that said breathable film has at least
       i) a WVTR in a range of from about 200 g/m$^2$/day to about 10,000 g/m$^2$/day at 38° C. and 90% relative humidity, wherein said WVTR of said breathable film produced is higher when said rollers are heated to the highest temperature within said temperature range than said WVTR of said breathable film produced at the lowest temperature within said temperature range,
       ii) a dart drop impact in a range of from about 100 grams to about 300 grams, and
       iii) an elongation selected from the group consisting of machine direction, transverse direction and combinations thereof in a range of from about 150% to about 550%.

7. The process of claim 6 wherein said polypropylene is selected from the group consisting of random copolymer polypropylene, impact copolymer polypropylene, polypropylene produced with a metallocene catalyst and combinations thereof.

8. The process of claim 6 wherein said elastomer is selected from the group consisting of styrene-isoprene-styrene, styrene-butadiene-styrene, styrene-ethylene-butylene-styrene, ethylene alpha-olefin rubber, ethylene propylene diene monomer rubber, butyl rubber, vulcanized natural rubber and combinations thereof.

9. The process of claim 6 wherein said plastomer is at least one ethylene α-olefin copolymer selected from the group consisting of ethylene α-olefin copolymers wherein the α-olefin comonomer is selected from the group consisting butene, pentene, hexene, and combinations thereof.

10. The process of claim 6 wherein said interdigitating grooved rollers are positioned in a direction selected from the group consisting of machine direction, transverse direction and combinations thereof.

11. The process of claim 6 futher comprising forming said film of step b) into a fabricated article selected from the group consisting of diapers, adult incontinence devices, surgical apparel, surgical drapes, sports apparel, industrial apparel, house wrap, filtration media and controlled atmosphere packaging.

12. The process of claim 6 wherein the precursor film has been embossed to impose thereon a pattern of multiple film thickness prior to having been passed between said at least one pair of interdigitating grooved rollers.

13. The process of claim 6 wherein the WVTR is greater than 1000 g/m$^2$/day at 38° C. and 90% relative humidity.

14. The process of claim 6 wherein the precursor film contacts the surface of one of the interdigitating grooved rollers that has been heated in the range of from 95° F. to 159° F. for at least one-fourth of a revolution before entering the nip between said pair of interdigitating grooved rollers providing for heating of the precursor film before entering the nip of the rollers.

15. The process of claim 6 wherein the initial basis weight of the precursor film is from 1.1 to 4 times the basis weight of the film after stretching.

16. The process of claim 6 wherein the initial basis weight of the precursor film is greater than the basis weight of the film after stretching.

17. The process of claim 6 wherein the precursor film is preheated and is at least 95° F. as the precursor film begins passing through said at least one pair of interdigitating grooved rollers.

18. The process of claim 6 wherein the second polymer composition comprises an elastomer.

\* \* \* \* \*